(12) United States Patent
Yamada et al.

(10) Patent No.: US 11,540,562 B2
(45) Date of Patent: Jan. 3, 2023

(54) INHALER DEVICE, AND METHOD AND PROGRAM FOR OPERATING THE SAME

(71) Applicant: JAPAN TOBACCO INC., Tokyo (JP)

(72) Inventors: Manabu Yamada, Tokyo (JP); Manabu Takeuchi, Tokyo (JP); Hirofumi Matsumoto, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 839 days.

(21) Appl. No.: 16/513,747

(22) Filed: Jul. 17, 2019

(65) Prior Publication Data

US 2019/0335816 A1 Nov. 7, 2019

Related U.S. Application Data

(63) Continuation of application No. PCT/JP2017/002221, filed on Jan. 24, 2017.

(51) Int. Cl.
| | | |
|---|---|---|
| *A24F 40/53* | (2020.01) | |
| *A24F 40/50* | (2020.01) | |
| *A61M 11/04* | (2006.01) | |
| *A61M 15/06* | (2006.01) | |
| *A24F 40/30* | (2020.01) | |

(Continued)

(52) U.S. Cl.
CPC ............ *A24F 40/50* (2020.01); *A24F 40/30* (2020.01); *A24F 40/53* (2020.01); *A24F 40/60* (2020.01); *A61M 11/042* (2014.02); *A61M 15/06* (2013.01); *A24B 15/167* (2016.11);
(Continued)

(58) Field of Classification Search
CPC ............................ A61M 11/042; A61M 15/06
See application file for complete search history.

(56) References Cited

U.S. PATENT DOCUMENTS

| | | |
|---|---|---|
| 4,682,010 A | 7/1987 | Drapeau et al. |
| 5,269,327 A | 12/1993 | Counts et al. |

(Continued)

FOREIGN PATENT DOCUMENTS

| | | |
|---|---|---|
| CN | 1106809 C | 4/2003 |
| CN | 104797151 A | 7/2015 |

(Continued)

OTHER PUBLICATIONS

Office Action dated Apr. 14, 2022 in Korean Patent Application No. 10-2021-7037621, 11 pages.

(Continued)

*Primary Examiner* — Neil Abrams
(74) *Attorney, Agent, or Firm* — Xsensus LLP

(57) ABSTRACT

An inhaler device including an atomizer configured to consume a first accumulated capacity and a second accumulated capacity to generate aerosol, and a light emitting diode (LED) configured to output a notification to an inhaler of the aerosol. The inhaler device further including circuitry configured to cause the LED to function in a first mode when the first accumulated capacity, detected or estimated, is smaller than a first threshold and the second accumulated capacity, detected or estimated, is equal to or larger than a second threshold, and cause the LED to function in a second mode different from the first mode when the first accumulated capacity is smaller than the first threshold and the second accumulated capacity is smaller than the second threshold.

20 Claims, 10 Drawing Sheets

(51) Int. Cl.
  *A24F 40/60* (2020.01)
  *A24B 15/167* (2020.01)
  *A24F 7/02* (2006.01)
  *A24F 40/10* (2020.01)
  *A24F 40/20* (2020.01)

(52) U.S. Cl.
  CPC .............. *A24F 7/02* (2013.01); *A24F 40/10* (2020.01); *A24F 40/20* (2020.01); *A61M 2205/8206* (2013.01)

(56) References Cited

U.S. PATENT DOCUMENTS

| | | | |
|---|---|---|---|
| 5,452,711 | A | 9/1995 | Gault |
| 6,155,268 | A | 12/2000 | Takeuchi |
| 9,462,832 | B2 | 10/2016 | Lord |
| 2011/0036346 | A1 | 2/2011 | Cohen et al. |
| 2014/0053856 | A1 | 2/2014 | Liu |
| 2015/0224268 | A1 | 8/2015 | Henry et al. |
| 2015/0245658 | A1* | 9/2015 | Worm ............... A24F 40/60 131/328 |
| 2015/0272223 | A1 | 10/2015 | Weigensberg et al. |
| 2015/0366266 | A1 | 12/2015 | Chen |
| 2016/0316821 | A1 | 11/2016 | Liu |
| 2017/0035114 | A1 | 2/2017 | Lord |
| 2017/0238606 | A1 | 8/2017 | Matsumoto et al. |
| 2017/0360097 | A1 | 12/2017 | Xiang |
| 2019/0335816 | A1* | 11/2019 | Yamada ............... A24F 40/53 |
| 2020/0282156 | A1* | 9/2020 | Potter ............... A61M 11/042 |
| 2021/0106064 | A1* | 4/2021 | Akao ............... A24F 40/57 |

FOREIGN PATENT DOCUMENTS

| | | |
|---|---|---|
| CN | 204682523 U | 10/2015 |
| CN | 204969463 U | 1/2016 |
| JP | 2014501106 A | 1/2014 |
| JP | 2014524313 A | 9/2014 |
| KR | 20-2015-0000824 U | 2/2015 |
| KR | 10-2016-0086118 A | 7/2016 |
| TW | 201626907 A | 8/2016 |
| WO | 2013025921 A1 | 2/2013 |
| WO | 2015/046386 A1 | 4/2015 |
| WO | 2015052513 A2 | 4/2015 |
| WO | 2015/109618 A1 | 7/2015 |
| WO | 2015130598 A2 | 9/2015 |
| WO | 2015/166952 A1 | 11/2015 |
| WO | 2016075747 A1 | 5/2016 |
| WO | 2016076178 A1 | 5/2016 |
| WO | 2016/101248 A1 | 6/2016 |
| WO | 2016/175320 A1 | 11/2016 |

OTHER PUBLICATIONS

Extended European Search Report dated Mar. 25, 2022, in corresponding European Patent Application No. 21197680.8.
Canadian Office Action dated Jul. 14, 2020, in corresponding Canadian Patent Application No. 3,037,654.
Office Action dated Jul. 26, 2021 in Chinese Patent Application No. 201780084587.0, 15 pages.
Office Action dated Aug. 20, 2019, issued in corresponding Taiwanese Patent Application No. 106123648, 26 pages (with English translation).
Office Action dated Aug. 19, 2019, issued in corresponding Japanese Patent Application No. 2018-242299, 14 pages (with English translation).
Office Action dated Apr. 24, 2020 in Taiwanese Patent Application No. 106123648, 23 pages.
International Search Report dated Mar. 28, 2017, issued in corresponding International Patent Application No. PCT/JP2017/002217, 10 pages.
International Search Report dated Mar. 28, 2017, issued in corresponding International Patent Application No. PCT/JP2017/002221, 12 pages.
Taiwanese Office Action dated Nov. 10, 2017, issued in corresponding Taiwanese Patent Application No. 106102622, 16 pages.
Japanese Office Action dated Aug. 23, 2018, issued in corresponding Japanese Patent Application No. 2018-540091, 10 pages.
Japanese Office Action dated Nov. 27, 2018, issued in corresponding Japanese Patent Application No. 2018-540091, 10 pages.
Japanese Office Action dated Apr. 2, 2019, issued in corresponding Japanese Patent Application No. 2018-242299, 15 pages.
Written Opinion and International Search Report of the International Searching Authority dated Mar. 28, 2017, issued in International Application No. PCT/JP2017/002214, 12 pages.
Japan Tobacco Inc., Starter Kit User Guide, 17 pages.

* cited by examiner

INHALER DEVICE, AND METHOD AND PROGRAM FOR OPERATING THE SAME

CROSS REFERENCE TO RELATED APPLICATIONS

The present application is a continuation application of International Application No. PCT/JP2017/002221, filed on Jan. 24, 2017. This application is related to co-pending U.S. application Ser. No. 16/395,326 filed on Apr. 26, 2019.

TECHNICAL FIELD

The present disclosure relates to an inhaler device that generates aerosol or aerosol imparted with flavor inhaled by a user, and a method and program for operating such an inhaler device.

BACKGROUND ART

In an inhaler device for generating aerosol inhaled by a user such as a general electronic cigarette or nebulizer, a sufficient inhaling experience cannot be provided to the user unless elements such as an aerosol source for generating the aerosol and a flavor source for imparting flavor to the aerosol are replaced for a specific number of times of inhaling.

As a solution to this problem, there is known a technique for urging the user to replace the elements by notifying the replacement of the elements to the user using a light emitting diode (LED) or the like. However, even if the notification is performed at a timing when the replacement of the aerosol source and the flavor source is necessary, the user does not always pay attention to the LED at that timing. Therefore, the user tends to overlook such a notification in a situation such as inhaling of the aerosol.

As another solution to this problem, PTL 1 discloses an electronic steam supply device that shifts to a sleep mode when a cumulative time of inhaling exceeds a predetermined threshold. However, the technique disclosed in PTL 1 does not visually make a notification to a user. Therefore, the technique does not always urge the user to replace the elements at appropriate timing.

In order to perform satisfactory inhaling using the general electronic cigarette or nebulizer, it is necessary to appropriately manage not only a residual amount of a battery that supplies electric power to an atomizing part but also a residual amount of the aerosol source for generating aerosol and a residual amount of the flavor source for imparting flavor to the aerosol. However, in these elements necessary for the inhaling of the aerosol, timings and frequencies for recovering the residual amounts are often greatly different because of characteristics and loaded capacities of the elements. Therefore, it is not easy for the user to recover the residual amounts of a plurality of these elements respectively at appropriate timings.

As a solution to this problem, PTL 2 discloses a technique for associating replacement timing of a first cartridge including an aerosol source and replacement timing of a second cartridge including a flavor source. However, there is still room of improvement in notifying, to allow the user to easily understand, necessity of recovery of the plurality of elements necessary for inhaling in which the timings and the frequencies for recovering the residual amounts are greatly different.

In the inhaler device such as the general electronic cigarette or nebulizer that provides an inhaling experience using the aerosol source for generating aerosol and the flavor source for imparting flavor to the aerosol, a sufficient inhaling experience cannot be provided to the user unless residual amounts of the aerosol source and the flavor source are appropriately managed. However, in the aerosol source and the flavor source, timings and frequencies for recovering the residual amounts are greatly different. Therefore, it is not easy to respectively appropriately manage the residual amounts of these elements.

As a solution to this problem, PTL 2 discloses a technique for reducing a burden for managing the residual amounts of these elements by associating replacement timing of a first cartridge including an aerosol source and replacement timing of a second cartridge including a flavor source. Further, PTL 2 discloses a technique for reducing the burden for managing the residual amounts of these elements in a similar manner by informing replacement timings of the first cartridge and the second cartridge as well. However, there is still room of improvement in that it is difficult to distinguish whether only the second cartridge has to be replaced or the first cartridge also needs to be replaced at the replacement timings of these elements. There is also still room of improvement in that, at the replacement timings of these elements, how the replacement timings should be informed to urge the user to recover the residual amounts of the plurality of elements such that the user can continuously inhale.

CITATION LIST

Patent Literature

PTL 1: WO 2015/052513
PTL 2: WO 2016/076178

SUMMARY OF INVENTION

Technical Problem

The present disclosure has been devised in view of the point described above.

A first problem to be solved by the present disclosure is to provide an inhaler device with which a user easily recognizes timings of replacement, filling, charging, and the like of an element necessary for inhaling of aerosol or aerosol imparted with flavor.

A second problem to be solved by the present disclosure is to provide an inhaler device that can reduce likelihood that a user neglects recovery of a residual amount of an element necessary for inhaling of aerosol or aerosol imparted with flavor.

A third problem to be solved by the present disclosure is to provide an inhaler device that can easily manage a residual amount of an element necessary for inhaling of aerosol or aerosol imparted with flavor.

Solution to Problem

In order to solve the first problem explained above, according to a first embodiment of the present disclosure, there is provided an inhaler device comprising: an element configured to consume an accumulated capacity to thereby contribute to generation of aerosol or aerosol imparted with flavor; a sensor configured to detect a predefined variable; a notifying part configured to make a notification to an inhaler of the aerosol; and a controller configured to cause the notifying part to function in a first mode when a detected or estimated capacity is smaller than a threshold and the variable satisfies a predefined condition for requesting the generation of the aerosol.

In an embodiment, the controller is configured to stop the generation of the aerosol when the controller causes the notifying part to function in the first mode.

In an embodiment, the condition is stricter when the capacity is smaller than the threshold than when the capacity is equal to or larger than the threshold.

In an embodiment, likelihood that the condition is satisfied is lower when the capacity is smaller than the threshold than when the capacity is equal to or larger than the threshold.

In an embodiment, the condition includes detection of the variable exceeding a predefined duration. The duration is longer when the capacity is smaller than the threshold than when the capacity is equal to or larger than the threshold.

In an embodiment, the condition includes detection of the variable having an absolute value exceeding a predefined value. The predefined value is larger when the capacity is smaller than the threshold than when the capacity is equal to or larger than the threshold.

In an embodiment, the notifying part includes a light emitting element. The controller is configured to cause the notifying part to function in a second mode during the generation of the aerosol. Light emission colors of the light emitting element in the first mode and the second mode are same. Light emission manners of the light emitting element in the first mode and the second mode are different.

In an embodiment, the notifying part includes a light emitting element. The controller is configured to cause the notifying part to function in a second mode during the generation of the aerosol. Light emission colors of the light emitting element in the first mode and the second mode are different. Light emission manners of the light emitting element in the first mode and the second mode are same.

In an embodiment, the inhaler device comprises a plurality of the elements. The controller is configured to cause, concerning only an element having a highest frequency of performing work for returning the element to a state having a capacity necessary for continuously generating the aerosol among the plurality of elements, the notifying part to function in the first mode only when the capacity is smaller than the threshold and the variable satisfies the predefined condition for requesting the generation of the aerosol.

In an embodiment, the controller is configured to cause the notifying part to function in a plurality of modes including the first mode and cause the notifying part to function for a longest time in the first mode among the plurality of modes.

In an embodiment, the inhaler device comprises a plurality of the elements. The controller is configured to cause, concerning only an element having a highest frequency of performing work for returning the element to a state having a capacity necessary for continuously generating the aerosol among the plurality of elements, the notifying part to function in the first mode only when the capacity is smaller than the threshold and the variable satisfies the predefined condition for requesting the generation of the aerosol.

In an embodiment, the controller is configured to presume that the capacity returns to a predetermined value after the function of the notifying part in the first mode ends.

In an embodiment, the controller is configured to count a number of times the capacity of the element returns to a predetermined value after the function of the notifying part in the first mode ends.

In an embodiment, the controller is configured to cause the notifying part to function in a plurality of modes including the first mode and cause the notifying part to function for a longest time in the first mode among the plurality of modes.

In an embodiment, the controller is configured to suspend the function of the notifying part when at least one of the elements is detached.

According to the first embodiment of the present disclosure, there is provided a method of operating an inhaler device, the method including: determining, concerning an element configured to consume an accumulated capacity to thereby contribute to generation of aerosol or aerosol imparted with flavor, whether a detected or estimated capacity is smaller than a threshold; determining whether a detected predefined variable satisfies a predefined condition for requesting the generation of the aerosol; and making a predetermined notification to an inhaler of the aerosol when the detected or estimated capacity is smaller than the threshold and the variable satisfies the predefined condition.

According to the first embodiment of the present disclosure, there is provided a program for, when being executed by a processor, causing the processor to execute the method.

In order to solve the second problem explained above, according to a second embodiment of the present disclosure, there is provided an inhaler device comprising: a plurality of elements configured to consume an accumulated capacity to thereby contribute to generation of aerosol or aerosol imparted with flavor; a notifying part configured to make a notification to an inhaler of the aerosol; and a controller configured to cause, concerning each element among the plurality of elements, the notifying part to function when a predefined condition set concerning the element including a requirement that a detected or estimated capacity is equal to or smaller than a threshold set concerning the element is satisfied. The condition is stricter for an element having a higher frequency of performing work for returning the element to a state having a capacity necessary for continuously generating the aerosol among the plurality of elements.

In an embodiment, the condition is less likely to be satisfied in the element having the higher frequency among the plurality of elements.

In an embodiment, the condition includes more requirements for the element having the higher frequency among the plurality of elements.

In an embodiment, the controller is further configured to acquire a request for the generation of the aerosol. The condition of the element having the highest frequency among the plurality of elements includes detection of the request.

In an embodiment, the controller is configured to cause, concerning the element having the higher frequency among the plurality of elements, the notifying part to function for a longer time when the condition is satisfied.

In an embodiment, the notifying part includes a light emitting element. The controller is configured to set different light emission colors of the light emitting element for the respective plurality of elements.

In an embodiment, the controller is configured to set, based on the frequencies of the respective plurality of elements, light emission colors of the light emitting elements for the respective plurality of elements.

In an embodiment, the notifying part includes a light emitting element. The controller is configured to set, concerning the element having the higher frequency among the plurality of elements, a light emission color of the light emitting element closer to a cold color.

In an embodiment, the controller is configured to control, concerning the element having the highest frequency among the plurality of elements, the light emitting element such that a light emission color of the light emitting element is same when the condition is satisfied and when the aerosol is being generated.

In an embodiment, the notifying part includes a light emitting element. The controller is configured to set, concerning the element having the lower frequency among the plurality of elements, a light emission color of the light emitting element closer to a warm color.

In an embodiment, the capacity of at least one element among the plurality of elements is detected or estimated by a method different from a method of detecting or estimating the capacity of at least one other element among the plurality of elements.

In an embodiment, the capacities of at least two elements among the plurality of elements are detected or estimated by a same method.

In an embodiment, the controller is configured to suspend the function of the notifying part when at least one of the elements is detached.

According to the second embodiment of the present disclosure, there is provided a method of operating an inhaler device, the method including: determining, concerning each of a plurality of elements configured to consume an accumulated capacity to thereby contribute to generation of aerosol or aerosol imparted with flavor, whether a predefined condition set concerning the element including a requirement that a detected or estimated capacity is equal to or smaller than a threshold set concerning the element is satisfied; and making a predetermined notification to an inhaler of the aerosol when the predefined condition is satisfied. The condition is stricter for an element having a higher frequency of performing work for returning the element to a state having a capacity necessary for continuously generating the aerosol among the plurality of elements.

According to the second embodiment of the present disclosure, there is provided a program for, when being executed by a processor, causing the processor to execute the method.

According to the second embodiment of the present disclosure, there is provided an inhaler device comprising: a plurality of elements configured to consume an accumulated capacity to thereby contribute to generation of aerosol or aerosol imparted with flavor; a notifying part configured to make a notification to an inhaler of the aerosol; and a controller configured to cause, concerning each element among the plurality of elements, the notifying part to function when a detected or estimated capacity is equal to or smaller than a threshold set concerning the element and a predefined condition set concerning the element is satisfied. The condition is stricter for an element having a higher frequency of performing work for returning the element to a state having a capacity necessary for continuously generating the aerosol among the plurality of elements.

According to the second embodiment of the present disclosure, there is provided a method of operating an inhaler device, the method including: determining, concerning each of a plurality of elements configured to consume an accumulated capacity to thereby contribute to generation of aerosol, whether a detected or estimated capacity is equal to or smaller than a threshold set concerning the element; determining whether a predefined condition set concerning the element is satisfied; and making a predetermined notification to an inhaler of the aerosol when the detected or estimated capacity is equal to or smaller than the threshold and the predefined condition is satisfied. The condition is stricter for an element having a higher frequency of performing work for returning the element to a state having a capacity necessary for continuously generating the aerosol among the plurality of elements.

According to the second embodiment of the present disclosure, there is provided a program for, when being executed by a processor, causing the processor to execute the method.

In order to solve the third problem explained above, according to a third embodiment of the present disclosure, there is provided an inhaler device comprising: first and second elements configured to consume an accumulated capacity to thereby contribute to generation of aerosol or aerosol imparted with flavor; a notifying part configured to make a notification to an inhaler of the aerosol; and a controller configured to cause the notifying part to function in a first mode when a first capacity detected or estimated concerning the first element is smaller than a first threshold and a second capacity detected or estimated concerning the second element is equal to or larger than a second threshold and cause the notifying part to function in a second mode different from the first mode when the first capacity is smaller than the first threshold and the second capacity is smaller than the second threshold. A frequency of performing work for returning the first element to a state having a capacity necessary for continuously generating the aerosol is higher than the frequency concerning the second element.

In an embodiment, the notifying part includes a light emitting element. The controller is configured to cause the light emitting element to emit light in different light emission colors in the first mode and the second mode.

In an embodiment, the controller is configured to set a light emission color of the light emitting element in the first mode closer to a cold color compared with the light emission color in the second mode.

In an embodiment, the controller is configured to cause the notifying part to function for different times in the first mode and the second mode.

In an embodiment, the controller is configured to set a time for causing the notifying part to function in the first mode short compared with the time in the second mode.

In an embodiment, the inhaler device further includes a sensor configured to detect a predefined variable. The controller is configured to cause the notifying part to function in the first mode when the first capacity is smaller than the first threshold, the second capacity is equal to or larger than the second threshold, and the variable satisfies a predefined condition for requesting the generation of the aerosol.

In an embodiment, the controller is configured to stop the generation of the aerosol when causing the notifying part to function in the first mode.

In an embodiment, the condition is stricter when the first capacity is smaller than the first threshold than when the first capacity is equal to or larger than the first threshold.

In an embodiment, likelihood that the condition is satisfied is lower when the first capacity is smaller than the threshold than likelihood that the condition is satisfied when the first capacity is equal to or larger than the threshold.

In an embodiment, the condition includes detection of the variable exceeding a predefined duration. The duration is longer when the first capacity is smaller than the first threshold than when the first capacity is equal to or larger than the first threshold.

In an embodiment, the condition includes detection of the variable having an absolute value exceeding a predefined value. The predefined value is larger when the first capacity is smaller than the first threshold than when the first capacity is equal to or larger than the first threshold.

In an embodiment, the controller is configured to cause the notifying part including a light emitting element to function in a third manner during the generation of the aerosol. Light emission colors of the light emitting element in the first mode and the third manner are same. Light emission manners of the light emitting element in the first mode and the third manner are different.

In an embodiment, the controller is configured to cause the notifying part including a light emitting element to function in a third manner during the generation of the aerosol. Light emission colors of the light emitting element in the first mode and the third manner are different. Light emission manners of the light emitting element in the first mode and the third manner are same.

In an embodiment, the controller is configured to presume that the first capacity returns to a predetermined value after the function of the notifying part in the first mode ends.

In an embodiment, the controller is configured to count a number of times the first capacity returns to a predetermined value after the function of the notifying part in the first mode ends.

In an embodiment, the inhaler device comprises a plurality of elements including at least the first and second elements and configured to consume an accumulated capacity to thereby contribute to generation of aerosol or aerosol imparted with flavor. The controller is configured to cause, concerning each element among the plurality of elements, the notifying part to function when a predefined condition set concerning the element including a requirement that a detected or estimated capacity is equal to or smaller than a threshold set concerning the element is satisfied. The condition is stricter for the element having the higher frequency among the plurality of elements.

In an embodiment, the condition is less likely to be satisfied for the element having the higher frequency among the plurality of elements.

In an embodiment, the condition includes more requirements for the element having the higher frequency among the plurality of elements.

In an embodiment, the controller is further configured to acquire a request for the generation of the aerosol. The condition for the element having the highest frequency among the plurality of elements includes detection of the request.

In an embodiment, the controller is configured to cause the notifying part to function for a longer time concerning the element having the higher frequency among the plurality of elements when the condition is satisfied.

In an embodiment, the controller is configured to differentiate and set light emission colors of a light emitting element included in the notifying part for the respective plurality of elements.

In an embodiment, the controller is configured to set, based on the frequencies of the plurality of elements, light emission colors of the light emitting element for the respective plurality of elements.

In an embodiment, the controller is configured to set a light emission color of a light emitting element included in the notifying part closer to a cold color for the element having the higher frequency among the plurality of elements.

In an embodiment, the controller is configured to control, concerning the element having the highest frequency among the plurality of elements, the light emitting element such that a light emission color of the light emitting element when the condition is satisfied and a light emission color of the light emitting element during the generation of the aerosol are same.

In an embodiment, the controller is configured to set a light emission color of a light emitting element included in the notifying part closer to a warm color for the element having the lower frequency among the plurality of elements.

In an embodiment, the capacity of at least one element among the plurality of elements and the capacity of at least one other element among the plurality of elements are detected or estimated by different methods.

In an embodiment, the capacities of at least two elements among the plurality of elements are detected or estimated by a same method.

In an embodiment, the inhaler device comprises a plurality of elements including at least the first and second elements and configured to consume an accumulated capacity to thereby contribute to generation of aerosol or aerosol imparted with flavor. The controller is configured to cause, concerning each element among the plurality of elements, the notifying part to function when a predefined condition set concerning the element including a requirement that a detected or estimated capacity is equal to or smaller than a threshold set concerning the element is satisfied. The condition is more permissive for the element having the lower frequency among the plurality of elements.

In an embodiment, the controller is configured to suspend the function of the notifying part when at least one element is detached.

According to the third embodiment of the present disclosure, there is provided a method of operating an inhaler device, the inhaler device comprising first and second elements configured to consume an accumulated capacity to thereby contribute to generation of aerosol or aerosol imparted with flavor, the method comprising: making a notification to an inhaler of the aerosol in a first mode when a first capacity detected or estimated concerning the first element is smaller than a first threshold and a second capacity detected or estimated concerning the second element is equal to or larger than a second threshold; and making a notification to the inhaler of the aerosol in a second mode different from the first mode when the first capacity is smaller than the first threshold and the second capacity is smaller than the second threshold. A frequency of performing work for returning the first element to a state having a capacity necessary for continuous generation of the aerosol is higher than the frequency concerning the second element.

According to the third embodiment of the present disclosure, there is provided a program for, when being executed by a processor, causing the processor to execute the method.

Advantageous Effects of Invention

According to the first embodiment of the present disclosure, it is possible to provide the inhaler device with which a user easily recognizes timings of replacement, filling, charging, and the like of an element necessary for inhaling of aerosol or aerosol imparted with flavor.

According to the second embodiment of the present disclosure, it is possible to provide the inhaler device with which a user easily understands recovery of residual amounts of a plurality of elements necessary for inhaling of aerosol or aerosol imparted with flavor.

According to the third embodiment of the present disclosure, it is possible to provide the inhaler device that can easily manage a residual amount of an element necessary for inhaling of aerosol or aerosol imparted with flavor.

DESCRIPTION OF EMBODIMENTS

Embodiments of the present disclosure are explained in detail below with reference to the drawings. Note that the embodiments of the present disclosure include an electronic cigarette and a nebulizer but are not limited to the electronic cigarette and the nebulizer. The embodiments of the present disclosure can include various inhaler devices for generating aerosol or aerosol imparted with flavor inhaled by a user.

Figure 1A:
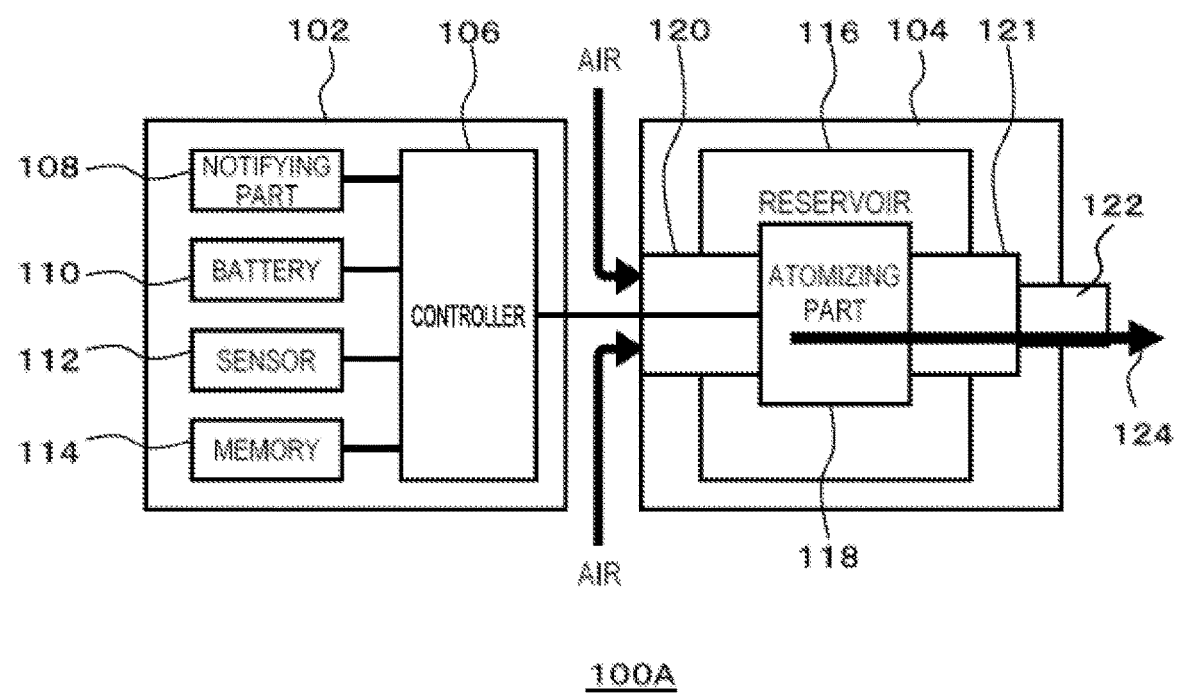
FIG. 1A is a schematic block diagram of the configuration of an inhaler device according to an embodiment of the present disclosure.

FIG. 1A is a schematic block diagram of the configuration of an inhaler device 100A according to an embodiment of the present disclosure. Note that FIG. 1A schematically and conceptually shows components included in the inhaler device 100A and does not show strict disposition, shapes, dimensions, positional relations, and the like of the components and the inhaler device 100A.

As shown in FIG. 1A, the inhaler device 100A includes a first member 102 and a second member 104. As shown in the figure, as an example, the first member 102 may include a controller 106, a notifying part 108, a battery 110, a sensor 112, and a memory 114. As an example, a second member 104 may include a reservoir 116, an atomizing part 118, an air intake channel 120, an aerosol flow path 121, and a suction port part 122. A part of the components included in the first member 102 may be included in the second member 104. A part of the components included in the second member 104 may be included in the first member 102. The second member 104 may be configured to be detachably attachable to the first member 102. Alternatively, all the components included in the first member 102 and the second member 104 may be included in the same housing instead of the first member 102 and the second member 104.

The reservoir 116 retains an aerosol source. For example, the reservoir 116 is formed of a fibrous or porous material. The reservoir 116 retains the aerosol source, which is liquid, in gaps among fibers or thin holes of a porous material. For example, cotton, glass fiber, a cigarette material or the like can be used as the fibrous or porous material. The reservoir 116 may be configured as a tank that stores liquid. The aerosol source is liquid, for example, polyalcohol such as glycerin or propylene glycol or water. When the inhaler device 100A is a medical inhaler such as a nebulizer, the aerosol source may include a drug to be inhaled by a patient. As another example, the aerosol source may include a cigarette material that emits a flagrance inhaling taste component by being heated or an extract deriving from the cigarette material. The reservoir 116 may include a component that can fill a consumed aerosol source. Alternatively, the reservoir 116 may be configured to be replaceable when the aerosol source is consumed. The aerosol source is not limited to the liquid and may be solid. When the aerosol source is the solid, the reservoir 116 may be, for example, a hollow container in which the fibrous or porous material is not used.

The atomizing part 118 is configured to atomize the aerosol source and generate aerosol. When an inhaling action is detected by the sensor 112, the atomizing part 118 generates aerosol. For example, a wick (not shown in the figure) may be provided to couple the reservoir 116 and the atomizing part 118. In this case, a part of the wick communicates with the inside of the reservoir 116 and is in contact with the aerosol source. Another part of the wick extends to the atomizing part 118. The aerosol source is carried from the reservoir 116 to the atomizing part 118 by a capillary effect of the wick. As an example, the atomizing part 118 includes a heater electrically connected to the battery 110. The heater is disposed in contact with or in close contact with the wick. When an inhaling action is detected, the controller 106 controls the heater of the atomizing part 118 and heats the aerosol source carried through the wick to thereby atomize the aerosol source. Another example of the atomizing part 118 may be an ultrasonic atomizer that atomizes the aerosol source with ultrasonic vibration. The air intake channel 120 is connected to the atomizing part 118. The air intake channel 120 communicates with the outside of the inhaler device 100. The aerosol generated in the atomizing part 118 is mixed with air taken in via the air intake channel 120. Mixed fluid of the aerosol and the air is delivered to the aerosol flow path 121 as indicated by an arrow 124. The aerosol flow path 121 has a tubular structure for transporting the mixed fluid of the aerosol and the air generated in the atomizing part 118 to the suction port part 122.

The suction port part 122 is located at a terminal end of the aerosol flow path 121 and configured to open the aerosol flow path 121 to the outside of the inhaler device 100A. The user holds the suction port part 122 in the user's mouth and inhales the air including the aerosol to thereby take the air including the aerosol into the oral cavity.

The notifying part 108 may include a light emitting element such as an LED, a display, a speaker, a vibrator or the like. The notifying part 108 is configured to perform some notification to the user with light emission, display, utterance, vibration, or the like according to necessity.

The battery 110 supplies electric power to the components of the inhaler device 100A such as the notifying part 108, the sensor 112, the memory 114, and the atomizing part 118. The battery 110 can also be charged by being connected to an external power supply via a predetermined port (not shown in the figure) of the inhaler device 100A. Only the battery 110 may be detachable from the first member 102 or the inhaler device 100A or may be replaceable with a new battery 110. The battery 110 may be replaceable with a new battery 110 by replacing the entire first member 102 with a new first member 102.

The sensor 112 may include a pressure sensor that detects fluctuation in pressure in the air intake channel 120 and/or the aerosol flow path 121 or a flow sensor that detects a flow rate in the air intake channel 120 and/or the aerosol flow path 121. The sensor 112 may include a weight sensor that detects the weight of a component such as the reservoir 116. The sensor 112 may be configured to count the number of times the user puffs using the inhaler device 100A. The sensor 112 may be configured to integrate an energization time to the atomizing part 118. The sensor 112 may be configured to detect the height of a liquid surface in the reservoir 116. The sensor 112 may be configured to detect an SOC (State of Charge), a current integrated value, a voltage, and the like of the battery 110. The current integrated value may be calculated by a current integration method, an SOC-OCV (Open Circuit Voltage) method, or the like. The sensor 112 may be an operation button or the like operable by the user.

The controller 106 may be an electronic circuit module configured as a microprocessor or a microcontroller. The controller 106 may be configured to control the operation of the inhaler device 100A in accordance with computer-executable instructions stored in the memory 114. The memory 114 is a storage medium such as ROM, RAM, flash memory or the like. In the memory 114, in addition to the above-mentioned computer executable instructions, setting data required for controlling the inhaler device 100A and the like may be stored. For example, the memory 114 may store a control method of the notifying part 108 (aspects, etc. of light emission, sound production, vibration, etc.), values detected by the sensor 112, and various pieces of data such as heating history of the atomizing part 118. The controller 106 reads data from the memory 114 as required to use it in control of the inhaler device 100A and stores data in the memory 114 as required.

Figure 1B:
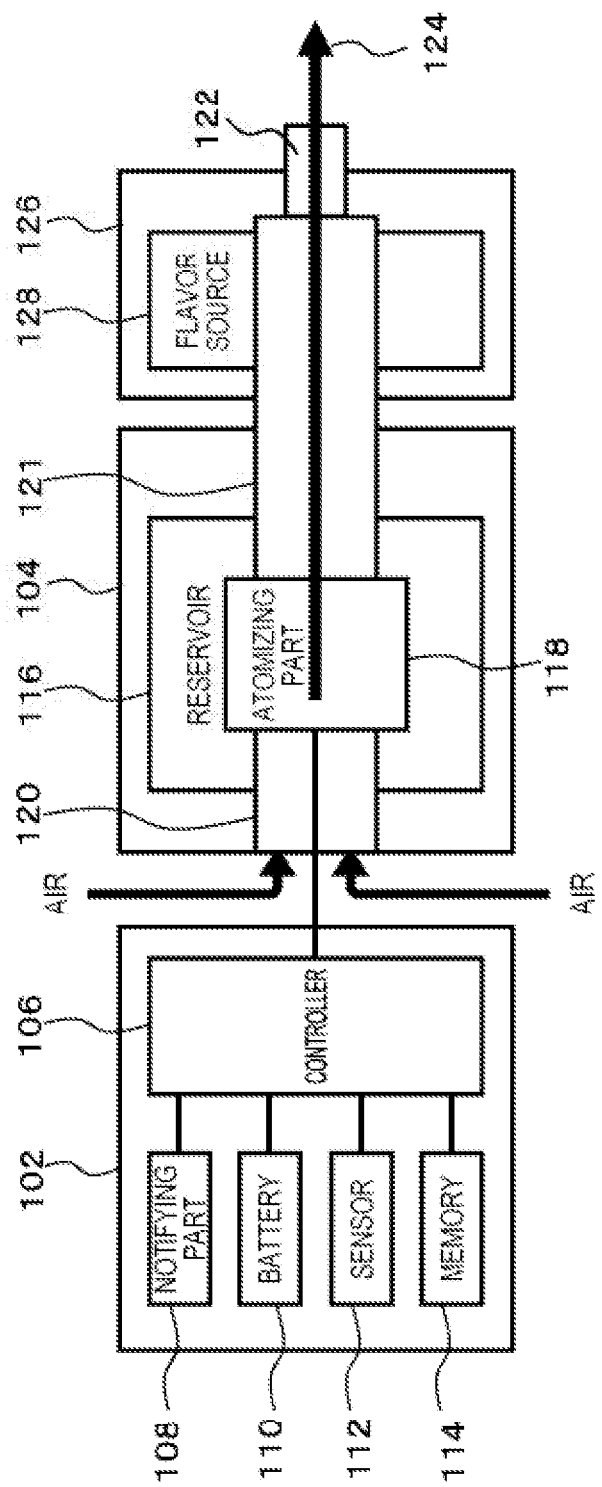
FIG. 1B is a schematic block diagram of the configuration of the inhaler device according to the embodiment of the present disclosure.

FIG. 1B is a schematic block diagram of the feature of the inhaler device 100B according to an embodiment of the present disclosure.

As shown in the figure, the inhaler device 100B includes a third member 126 in addition to the features which the inhaler device 100A of FIG. 1A includes. The third member 126 may include a flavor source 128. As an example, if the inhaler device 100B is an electronic cigarette, the flavor source 128 may include flavoring ingredients contained in tobacco. As illustrated in the figure, the aerosol flow path 121 extends from the second member 104 to the third member 126. The suction port part 122 is included in the third member 126.

The flavor source 128 is a component for imparting flavor to the aerosol. The flavor source 128 is placed in the middle of the aerosol flow path 121. A mixed fluid of aerosol and air (hereinafter, the mixed fluid may be simply referred to as "aerosol" in some cases) generated by the atomizing part 118 flows through the aerosol flow path 121 to the suction port part 122. In this manner, the flavor source 128 is provided downstream of the atomizing part 118 with respect to the aerosol flow. In other words, the flavor source 128 is located closer to the suction port part 122 in the aerosol flow path 121 than the atomizing part 118. Accordingly, the aerosol generated by the atomizing part 118 passes through the flavor source 128 and then reaches the suction port part 122. As the aerosol passes through the flavor source 128, the aerosol is imparted with the flavoring ingredients contained in the flavor source 128. As an example, if the inhaler device 100B is an electronic cigarette, the flavor source 128 may be derived from tobacco such as shredded tobacco or a processed product obtained by forming a tobacco material into a particulate, sheet-like, or powder-like form. The flavor source 128 may also be derived from material other than tobacco made from plants different than tobacco (for example, mint, herb, etc.). As an example, the flavor source 128 contains nicotine components. The flavor source 128 may contain perfume ingredients such as menthol. In addition to the flavor source 128, the reservoir 116 may also have substances containing flavoring ingredients. For example, the inhaler device 100B may retain flavoring substances derived from tobacco in the flavor source 128 and may be configured to contain flavoring substances that are not derived from tobacco in the reservoir 116.

By putting the suction port part 122 in the mouth for inhaling, the user can take in the air containing the aerosol imparted with flavor into his/her mouth.

The controller 106 is configured to control the inhaler devices 100A and 100B (which may be hereinafter generically referred to as "inhaler device 100") according to the embodiments of the present disclosure in various methods. Each embodiment will be described in detail below.

First Embodiment

Figure 2:
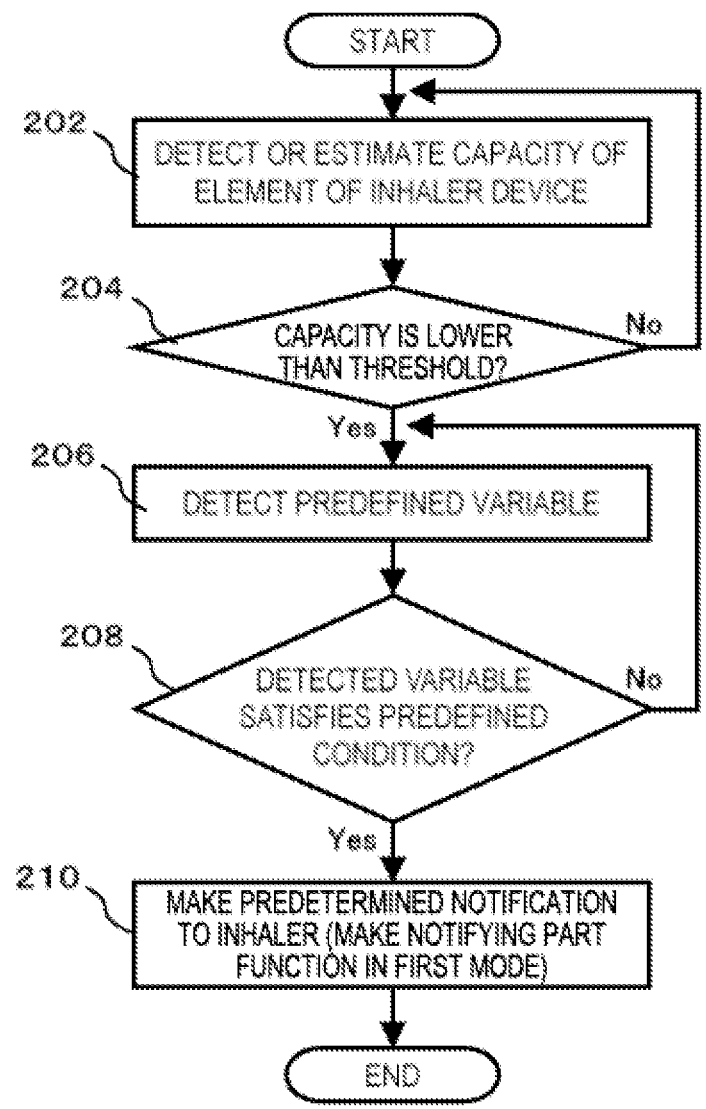
FIG. 2 is a flowchart showing a basic operation of an inhaler device according to a first embodiment of the present disclosure.

FIG. 2 is a flowchart that shows the basic operation of the inhaler device 100 according to the first embodiment of the present disclosure. In the following description, the controller 106 will be described as performing all the steps shown in FIG. 2. However, it should be noted that some steps of FIG. 2 may be performed by other components in the inhaler device 100.

In the step 202, the controller 106 detects or estimates the capacity of the elements of the inhaler device 100. Here, "element" means a component that is configured to contribute to the generation of aerosol or aerosol imparted with flavor by consuming the accumulated capacity. As an example, in the case of the electronic cigarette having the configuration of the inhaler device 100A shown in FIG. 1A, the first member 102 can be provided as a battery accommodation unit that includes the battery 110 while the second member 104 can be provided as a cartridge that includes the reservoir 116. In this case, the battery accommodation unit (or the battery 110) and the cartridge (or the reservoir 116) correspond to the above-mentioned "elements." Here, "capacity" means the residual amount of the battery 110, the residual amount of the aerosol source included in the reservoir 116, and the like. As another example, in the case of the electronic cigarette having the configuration of the inhaler device 100B shown in FIG. 1B, the first member 102 can be provided as a battery accommodation unit that includes the battery 110, the second member 104 can be provided as a cartridge that includes the reservoir 116, and the third member 126 can be provided as a capsule that includes the flavor source 128. In this case, the battery accommodation unit (or the battery 110), the cartridge (or the reservoir 116), and the capsule (or the flavor source 128) correspond to the "elements." Here, "capacity" means the residual amount of the battery 110, the residual amount of the aerosol source in the reservoir 116, the residual amount of the flavoring ingredients included in the flavor source 128, that of the aerosol source, and the like. The volume, weight, etc. of the flavor source 128 and the reservoir 116 can increase in accordance with the use of the inhaler device 100. Accordingly, it should be noted that the volume, weight, etc. of the flavor source 128 and the reservoir 116 do not necessarily correspond to the "capacity."

The capacities of the elements can be detected or estimated by various methods. In one example, the sensor 112 may be a weight sensor. In this case, the controller 106 may detect, using the sensor 112, the weight of the element (for example, the weight of liquid or tobacco in the case where the aerosol source included in the reservoir 116 is liquid or tobacco) and determine the weight that has been detected as the capacity of this element. In another example, the sensor 112 may be capable of detecting the level of a liquid surface (of the aerosol source included in the reservoir 116 or the like). In this case, the controller 106 may detect, using the sensor 112, the level of the liquid surface of an element and estimate the capacity of this element on the basis of the level of the liquid surface that has been detected. In another example, the memory 114 may store the cumulative value of the energization time for the atomizing part 118. In this case, the controller 106 may estimate the capacity of the element (for example, the residual amount of the aerosol source included in the reservoir 116, the residual amount of the flavoring ingredients of tobacco, the residual amount of the flavoring ingredients contained in the flavor source 128, and the like) on the basis of the cumulative energization time acquired from the memory 114. In another example, the memory 114 may store the number of times of inhaling that the user performed on the inhaler device 100 ("puffing" in the case of an electronic cigarette). In this case, the controller 106 may estimate the capacity of the element on the basis of the number of times of inhaling acquired from the memory 114. In another example, the memory 114 may store data regarding the heating history of the atomizing part 118. In this case, the controller 106 may estimate the capacity of the element on the basis of the data acquired from the memory 114. In another example, the memory 114 may store data regarding the state of charge (SOC) of the battery 110, a cumulative current value and/or voltage. The sensor 112 may detect these values. In this case, the controller 106 can detect or estimate the capacity of the elements (in particular, the battery 110) on the basis of these pieces of data.

In the step 204, the controller 106 determines whether or not the capacity of the element that has been detected or estimated in the step 202 is lower than a threshold. The threshold may be stored in the memory 114 or the controller 106 may acquire the threshold from the memory 114. If the capacity is not smaller than the threshold ("No" in the step 204), the processing goes back to the stage before the step 202. If the capacity is smaller than the threshold ("Yes" in the step 204), the processing proceeds to the step 206.

In the step 206, the controller 106 detects a predefined variable. In one example, if the sensor 112 includes a pressure sensor that detects the pressure in the air intake flow path 120 and/or the aerosol flow path 121, then the predefined variable may be pressure. In another example, if the sensor 112 includes a flow sensor that detect the flow rate in the air intake flow path 120 and/or the aerosol flow path 121 in place of the pressure in the paths, the predefined variable may be flow rate. In another example, if the inhaler device 100 includes a button (not shown) for driving, then the predefined variable may be stress, current value, or the like indicative of the fact that the button has been pressed.

Note that the sensor 112 may include a plurality of sensors, where at least two of the sensors may detect different physical quantities. In the step 202, the controller 106 may use a part of the sensors in order to detect or estimate the capacity of the element of the inhaler device 100. Further, in the step 206, the controller 106 may use a different part of the sensors in order to detect the predefined variable.

In the step 208, the controller 106 determines whether or not the variable that has been detected in the step 206 satisfies a predefined condition. Here, the predefined condition can be defined as a condition needed to issue a request for generation of aerosol in the inhaler device 100. In one example, if the variable is pressure or flow rate, the predefined condition may be that a pressure or flow rate is detected beyond a predetermined duration. In another example, if the variable is pressure or flow rate, the predefined condition may be that a pressure or flow rate having an absolute value exceeding a predefined value is detected. It will be appreciated that, in the embodiments as well where the variable is another value other than the pressure, various conditions can be specified as the predefined condition. If the variable that has been detected does not satisfy the predefined condition ("No" in the step 208), then the processing goes back to the stage before the step 206. If the variable that has been detected satisfies the predefined condition ("Yes" in the step 208), then the processing proceeds to the step 210.

In the step 210, the controller 106 performs a predetermined notification to the user (that is, an inhaler of the inhaler device 100). For example, the controller 106 causes the notifying part 108 to function in a first mode having a predetermined manner. In one example, if the notifying part 108 includes an LED, the controller 106 may cause the LED to operate in a predetermined manner (for example, blinking). In another example, if the notifying part 108 includes a display, the controller 106 may cause the display to operate so as to perform predetermined indication indicative of the fact that replacement, filling, charging, etc. of elements (which is hereinafter referred to as "replacement, etc." as required) is necessary. As another example, if the notifying part 108 includes a speaker, the controller 106 may cause the speaker to operate so as to output a predetermined sound.

Figure 3:
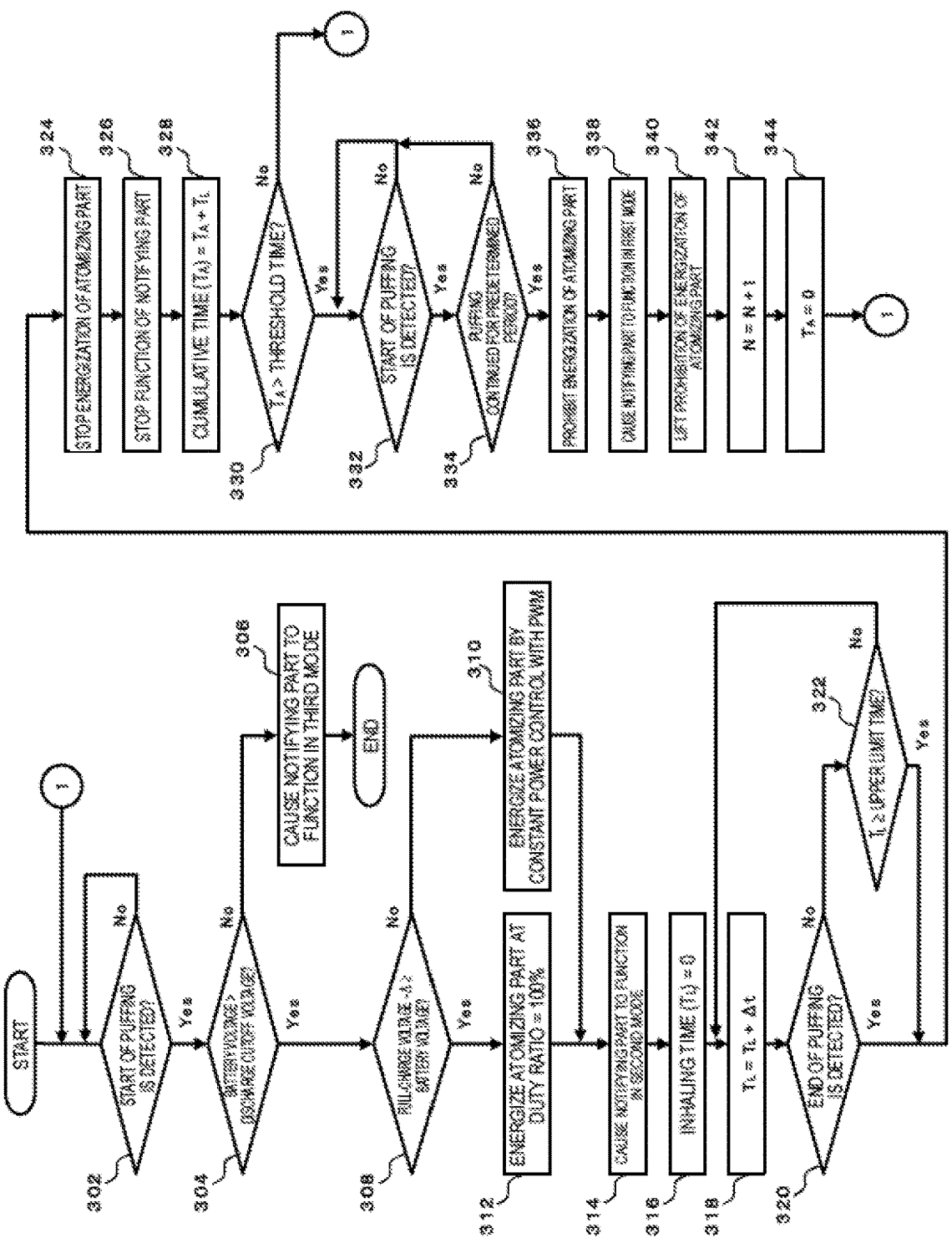
FIG. 3 is a flowchart showing, in detail, an example of the operation of the inhaler device according to the first embodiment of the present disclosure.

FIG. 3 is a flowchart showing in detail an example of the operation of the inhaler device 100 according to this embodiment. In the following description, the controller 106 will be described as executing all the steps shown in FIG. 3. However, it should be noted that some steps of FIG. 3 may be performed by other components in the inhaler device 100. Here, explanations will be provided on the assumption that the inhaler device has the features of the inhaler device 100B shown in FIG. 1B and the third member 126 (including the flavor source 128) of the inhaler device 100B is the "element" which has been described in relation to FIG. 2. However, the embodiments of the present disclosure are not limited to such a configuration and it should be noted that the first member 102 (or the battery 110) and the second member 104 (or the reservoir 116) may be the "element."

The processing starts with the step 302. In the step 302, the controller 106 determines whether or not start of puffing of the inhaler device 100 by the user has been detected. As an example, if the sensor 112 includes a pressure sensor or a flow sensor, the controller 106 may determine that the puffing has been started when the pressure or flow rate acquired from the sensor 112 exceeded a predefined value. The controller 106 may also determine that the puffing has been started when the duration in which the pressure is detected by the sensor 112 exceeds a predetermined duration. In another example, the controller 106 may determine that the puffing has been started when the inhaler device 100 includes a start button and the button has been pressed. If the start of the puffing is not detected ("No" in the step 302), the processing goes back to the stage before the step 302. If the start of the puffing has been detected ("Yes" in the step 302), then the processing proceeds to the step 304.

In the step 304, the controller 106 determines whether or not the voltage of the battery 110 is larger than the discharge cutoff voltage (for example, 3.2 V). If the voltage of the battery 110 is equal to or lower than the discharge cutoff voltage ("No" in the step 304), the processing proceeds to the step 306. In the step 306, the controller 106 causes the notifying part 108 to function in the third manner. In one example, if the notifying part 108 includes an LED, the third manner may include causing the LED to blink in red. On the other hand, if the voltage of the battery 110 is larger than the discharge cutoff voltage ("Yes" in the step 304), the processing proceeds to the step 308.

In the step 308, the controller 106 determines whether or not the voltage of the battery 110 is equal to or lower than the value obtained by subtracting a predetermined value from the full-charge voltage. If the voltage of the battery 110 is not equal to or lower than "full-charge voltage−Δ" ("No" in the step 308), the relationship will be "full-charge voltage−Δ<battery voltage≤full-charge voltage." At this point, the processing proceeds to the step 310. In the step 310, the controller 106 energizes the atomizing part 118 by constant power control. For example, the controller 106 may carry out pulse width modulation (PWM) on the power supplied from the battery 110 to the atomizing part 118 and may adjust the pulse width in accordance with the change in the output voltage of the battery 110 such that the value of the power supplied to the atomizing part 118 becomes constant. Note that the controller 106 may implement pulse frequency modulation (PFM) control in place of the pulse width modulation (PWM) control. On the other hand, if the voltage of the battery 110 is equal to or lower than "full-charge voltage−Δ" ("Yes" in the step 308), the processing proceeds to the step 312. In the step 312, the controller 106 does not carry out the pulse width modulation on the power from the battery 110 and energizes the atomizing part 118 at a duty ratio=100%.

The processing proceeds to the step 314 and the controller 106 causes the notifying part 108 to function in the second mode. In one example, if the notifying part 108 includes an LED, the controller 106 may cause the LED to be lit in blue.

The processing proceeds to the step 316 and the controller 106 sets the inhaling time ($T_L$), which can be stored in the memory 114, the controller 106, etc., to 0.

The processing proceeds to the step 318 and the controller 106 waits until the predetermined time Δt elapses, and sets $T_L$ to "$T_L=T_L+\Delta t$."

The processing proceeds to the step 320 and the controller 106 determines whether or not the end of the puffing has been detected. In one example, if the sensor 112 includes a pressure sensor, the controller 106 may determine that the puffing has ended when the pressure acquired from the sensor 112 becomes equal to or lower than a predetermined value. When the end of the puffing has been detected ("Yes" in the step 320), the processing proceeds to the step 324. When the end of the puffing is not detected ("No" in the step 320), the processing proceeds to the step 322 and the controller 106 determines whether or not $T_L$ is equal to or longer than the predetermined upper limit time. If $T_L$ is not equal to or longer than the predetermined upper limit time ("No" in the step 322), the processing goes back to the stage before the step 318. If $T_L$ is equal to or longer than the predetermined upper limit time ("Yes" in the step 322), the processing proceeds to the step 324.

In the step 324, the controller 106 stops energization of the atomizing part 118, for example, by controlling a switch provided in the electrical circuit interconnecting the battery 110 and the atomizing part 118.

The processing proceeds to the step 326 and the controller 106 stops the function of the notifying part 108. In one example, the controller 106 turns off the LED of the notifying part 108 which has been lit in blue.

Note that, if the end of the puffing is not detected ("No" in the step 320) and $T_L$ is equal to or longer than the predetermined upper limit time ("Yes" in the step 322), the controller 106 may continue the function of the notifying part 108 in the second mode (for example, the mode at the time of normal inhaling) until the end of the puffing is detected after the energization of the atomizing part 118 was stopped in the step 324. After that, in the step 326, the controller 106 stops the function of the notifying part 108. Since the notifying part 108 continues to function in the second mode as long as the puffing continues, it is made possible to stop the aerosol generation and suppress decrease in the user experience which may cause the user to develop a feeling of strangeness.

The processing proceeds to the step 328 and the controller 106 sets the cumulative time $T_A$, which can be stored in the memory 114, the controller 106, etc., to "$T_A=T_A+T_L$."

The processing proceeds to the step 330. The step 330 is an example of the step 204 of FIG. 2. In the step 330, the controller 106 determines whether or not $T_A$ is longer than a predetermined threshold time. The threshold time can be defined as the cumulative time of the inhaling on the inhaler device 100B at which it is estimated that the capacity (in this example, the residual amount of the flavoring ingredients contained in the flavor source 128) of the element of the inhaler device 100B (in this example, the third member 126 or flavor source 128) is lower than the value necessary for generating aerosol imparted with sufficient flavor. The threshold time may be stored in advance in the memory 114, etc.

If $T_A$ is equal to or shorter than the threshold time ("No" in the step 330), the processing goes back to the stage before the step 302. If $T_A$ is longer than the threshold time ("Yes" in the step 330), the processing proceeds to the step 332.

The steps 332 and/or 334 are an example of the step 208 of FIG. 2. In the step 332, the controller 106 determines whether or not the start of the puffing has been detected. In one example, if the sensor 112 includes a pressure sensor or a flow sensor, the controller 106 may determine that the puffing has been started when the pressure or flow rate acquired from the sensor 112 has an absolute value exceeding a predefined value.

If the start of the puffing is not detected ("No" in the step 332), the processing goes back to the stage before the step 332. Specifically, the controller 106 waits for the start of the puffing being detected. If the start of the puffing has been detected ("Yes" in the step 332), the processing proceeds to the step 334.

In the step 334, the controller 106 determines whether or not the puffing continues for a predetermined period of time (for example, one second). The predetermined period of time may be stored in the memory 114. If the puffing does not continue for a predetermined period of time ("No" in the step 334), the processing goes back to the stage before the step 332. If the puffing has continued for the predetermined period of time ("Yes" in the step 334), the processing proceeds to the step 336. By performing the step 334, it is made possible to prevent the subsequent processes from being performed even when it has been erroneously determined that the start of the puffing was detected in the step 332 due to occurrence of background noise.

Both of the processes at the steps 332 and 334 may be performed and only either of them may be performed.

Since the controller 106 is configured to perform the steps 332 and 334, it is made possible to cause the notifying part 108 to function in the first mode on the basis of not only the excess of the cumulative time but also the subsequent puffing detection. Accordingly, since the notifying part 108 functions in the first mode at the point of time at which the user has attempted to smoke or do some action of this sort using the inhaler device 100, the user will more easily notice the fact that the element having a small capacity has to be replaced.

In the step 336, the controller 106 prohibits energization of the atomizing part 118. Note that the process at the step 336 may be performed between the step 330 and the step 332.

The processing proceeds to the step 338 and the controller 106 causes the notifying part 108 to function in the first mode. Since the controller 106 prohibits energization of the atomizing part 118 when causing the notifying part 108 to function in the first mode, it is made possible to stop the generation of the aerosol. For stoppage of the generation of the aerosol, the controller 106 may disable the sensor 112 or open the power supply circuit to the atomizing part 118. Since user's attention is aroused by the stoppage of the generation of the aerosol, the user will more easily notice the fact that replacement, etc. of the element is necessary. In addition, since it is possible to prevent generation of incomplete aerosol when the capacity of the element is insufficient, it is made possible to prevent user's inhaling experience from being impaired. In one example, if the notifying part 108 is an LED, the first mode may include causing the LED to blink in blue. The controller 106 may cause the notifying part 108 to function for a relatively long time (for example, 40 seconds) so that the user can notice the fact that the capacity of the element is insufficient.

In the step 338, the conditions of the steps 332 and 334 which are conditions for causing the notifying part 108 to function in the first mode may be stricter than the condition of the step 302 which is a condition for causing the notifying part 108 to function in the second mode in the step 314. Alternatively, the possibility that the conditions of the steps 332 and 334 are satisfied may be lower than the possibility that the condition of the step 302 is satisfied. For example, the above-mentioned predefined value used in the determination at the step 334 may be greater than the predefined value used in the determination at the step 302. By performing the above-described step 334, through the steps 332 and 334, at least continuation of the puffing for the above-mentioned predetermined time in the step 334 is required, so that the duration used in the determination of the puffing in the steps 332 and 334 which is the condition for causing the notifying part 108 to function in the first mode in the step 338 may be longer than the duration that is used in the determination at the step 302 which is the condition for causing the notifying part 108 to function in the second mode in the step 314. By virtue of these features, at the time of normal inhaling, it is made possible to improve aerosol generation response to user's puffing action and provide inhaling experience without any feeling of strangeness. Also, it is made possible to prevent the inhaler device 100 from erroneously performing normal operation due to background noise when the notifying part 108 has to function in the first mode. Also, the aerosol is not generated even when the puffing is performed for a longer period of time than that at the time of energization of the atomizing part 118, and the notification is performed in the step 338 after that, so that it is made possible for the user to notice the fact that recovery of the capacity is necessary in the state where the user is doubtful about the operation of the inhaler device 100, in other words, in the state where the user pays attention to the inhaler device 100.

If the notifying part 108 includes a light emitting element such as an LED, in the first mode at the step 338 and the second mode at the step 314, light emission colors of the light emitting element may be the same. For example, both emission colors may be blue. At this point, in the first mode and the second mode, the light emission manners by the light emitting element may be different. For example, the light emitting element may blink in the first mode and may be lit constantly in the second mode. Also, in another example, the light emission colors of the light emitting element may be different between the first mode and the second mode while the light emission manners by the light emitting element may be the same in both of these modes. Further, in another example, the light emission colors and the light emission manners of the light emitting element may be both different between the first mode and the second mode. By virtue of these features, when the light emitting element performs operation different than that in the normal state, the user can recognize that some abnormality associated with inhaling has occurred, so that it will be easier to urge the user to perform replacement, etc. of the element.

The processing proceeds to the step 340 and the controller 106 lifts the prohibition on the energization of the atomizing part 118. At this point, the controller 106 may estimate that the capacity of the element has been returned to a predetermined value (for example, a value sufficient for generation of the aerosol or aerosol imparted with flavor). Since a notification that the users is unlikely to overlook has already been performed by the notifying part 108, it is likely that the replacement, etc. has been performed on the element whose capacity was insufficient after completion of the function of the notifying part 108 in the first mode. As a result, the need for use of control logics and devices for fitting detection or switching is eliminated, which should only be used for the purpose of detecting whether or not the replacement, etc. of the element has been performed. Also, the accuracy of cumulative time and the counting of the number of times of replacement can be increased.

The processing proceeds to the step 342 and the controller 106 counts the number of times (N) by which the capacity of the element is returned to the predetermined value. N may be stored in the memory 114. The controller 106 may increment N by 1. By virtue of this feature, it is made possible to count the number of times of replacement of the above-described element which is a parameter useful in estimating the product life of the inhaler device 100, the degree of wear of other elements, and the like without using control logics and devices for fitting detection or switching, which should only be used for the purpose of detecting whether or not the replacement, etc. of the element has been performed. Note that N does not always need to be an integer and, instead, a real number may be used. Also, when N is to be compared with a particular value, the dimension of N may be a percentage (%).

The processing proceeds to the step 344 and the controller 106 reset the cumulative time $T_A$ (which is set to 0). The processing goes back to the stage before the step 302.

As has been described in relation to FIGS. 1A and 1B, the inhaler device 100 may include a plurality of elements. For example, the inhaler device 100A includes, as the elements, the first member (for example, the battery accommodation unit) 102 (or the battery 110) and the second member (for example, the cartridge) 104 (or the reservoir 116). The inhaler device 100B further includes the third member (for example, capsule) 126 (or flavor source 128) as its element. The controller 106 may perform the processing shown in FIG. 2 and the processing of the step 328 to the step 344 of FIG. 3 only with regard to the one of the plurality of elements on which the work for returning the capacity of the one element at issue to the state where it has the capacity needed to continuously generate the aerosol or aerosol imparted with flavor should be more frequently performed. For example, in the example of FIG. 1A, if the frequency of replacement of the second member 104 (or the reservoir 116) is higher than the frequency of charging of the battery 110 in the first member 102, the controller 106 may be configured to cause the notifying part 108 to function in the first mode only when the capacity of the second member 104 is smaller than a predetermined threshold ("Yes" in the step 204) and the variable (such as the pressure or flow rate detected by the sensor 112) satisfies the predefined condition for requesting generation of the aerosol or aerosol imparted with flavor ("Yes" in the step 208). Likewise, in the example of FIG. 1B, when the third member 126 (or flavor source 128) needs to be replaced more frequently than the first member 102 and the second member 104, the controller 106 may perform the processing of FIG. 2 only with regard to the third member 126. By virtue of this feature, when the notifying part 108 has performed operation different than that in the normal state, the user can recognize that a certain operation is needed on the element having the highest frequency of replacement regarding the inhaling, so that it becomes easier to urge the user to perform the replacement, etc. of the element.

As has been described in relation to FIG. 3, the controller 106 may be configured to cause the notifying part 108 to function in a plurality of modes including the first mode (the first, second, and third manners). In this case, the controller 106 may cause the notifying part 108 to function for the longest period of time in the first mode among these modes. By virtue of this feature, the operation time of the notifying part 108 for requesting the replacement, etc. of the element becomes longer than the operation times of the notifying part 108 in the other situations, so that it is made possible to reduce the possibility that the user overlook the necessity of the replacement, etc. of the element.

If the inhaler device 100 includes a plurality of elements, the controller 106 may be configured to suspend the function of the notifying part 108 when at least one element has been removed from the inhaler device 100. For example, if the inhaler device has the features of the inhaler device 100A shown in FIG. 1A and the second member 104 is removable, then the controller 106 may suspend the function of the notifying part 108 when the second member 104 has been removed. Likewise, if the inhaler device has the features of the inhaler device 100B shown in FIG. 1B and the second member 104 and the third member 126 are removable, then the controller 106 may suspend the function of the notifying part 108 when either or both of these members have been removed. In such a state where at least one element has been removed from the inhaler device 100, this state can be regarded as the state where the user has already recognized the notification of the notifying part 108. Hence, when the function of the notifying part 108 is suspended, the wasteful power consumption of the battery 110 can be avoided.

Note that the controller 106 may not include a part of the steps shown in FIG. 3 or the order of the part of the steps may be modified. For example, whether or not the start of the puffing has been detected may not be determined in the step 302 before the notifying part is made to function in the third manner in the step 306. In other words, the controller may perform the step 302 after the controller has determined in the step 304 whether or not the voltage of the battery 110 is equal to or lower than the discharge cutoff voltage. In this embodiment, it will be clearly appreciated that the condition that should be satisfied to cause the notifying part 108 to function in the third manner in relation to the battery 110 at the step 306 includes only one requirement that the voltage of the battery 110 is equal to or lower than the discharge cutoff voltage.

Alternatively, the controller 106 may always continue the determination at the step 304 in the processes at and after the step 302. That is, in the course of performing the steps 308 to 344, when the voltage of the battery 110 that the controller 106 detects becomes equal to or lower than the discharge cutoff voltage ("Yes" in the step 304), then the step 306 is performed as interrupt processing and the controller 106 causes the notifying part 108 to function in the third manner. In this embodiment, the condition that should be satisfied for causing the notifying part 108 to function in the third manner in relation to the battery 110 at the step 306 includes the requirement of whether or not the detection of puffing in the step 302 has been started. However, this requirement is a relatively moderate one only requiring that the step 304 should be satisfied at either of the steps after "Yes" was obtained by the determination at the step 302. In contrast, the condition that should be satisfied to cause the notifying part 108 to function in the first mode in the step 338 includes a relatively strict requirement that the controller 106 obtained "Yes" by its determination in relation to the steps 332 and 334 immediately after the controller 106 at the step 330 determined that the cumulative time $T_A$ is longer than the predetermined threshold time ("Yes" in the step 330). In other words, the step 306 is a process that can be performed during the aerosol generation, whereas the step 338 is a process that cannot be satisfied during the aerosol generation.

In the foregoing explanations, the first embodiment of the present disclosure has been described as the inhaler device having the features shown in FIG. 1A or 1B and the method shown in FIG. 2 or 3. However, it will be appreciated that the present disclosure, when executed by a processor, can be implemented as a program that causes the processor to perform the method shown in FIG. 2 or 3 or as a computer readable storage medium storing the same program.

Second Embodiment

Figure 4:
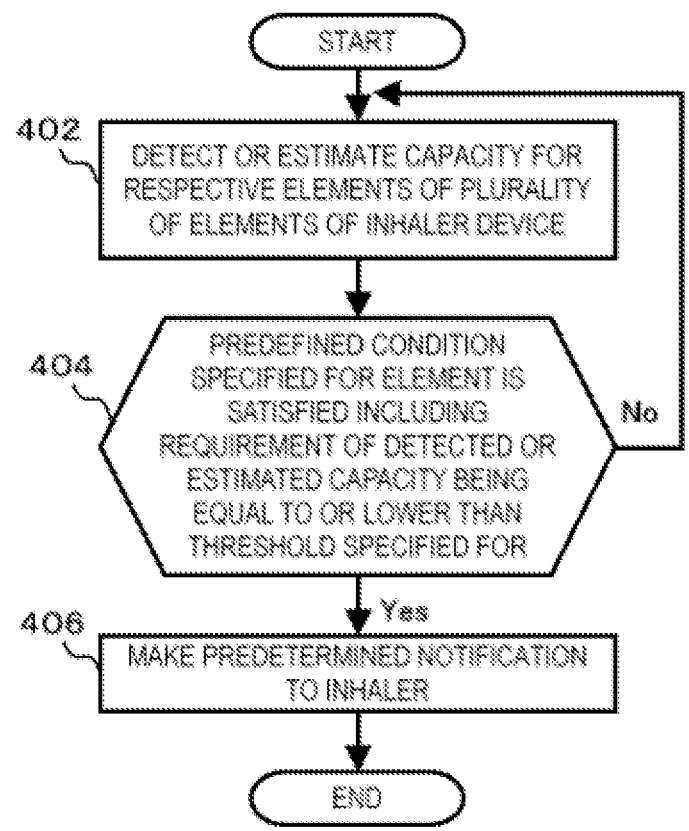
FIG. 4 is a flowchart showing a basic operation of an inhaler device according to a second embodiment of the present disclosure.

FIG. 4 is a flowchart that shows the basic operation of the inhaler device 100 according to the second embodiment of the present disclosure. In the following description, the controller 106 will be described as executing all the steps shown in FIG. 4. However, it should be noted that some steps of FIG. 4 may be performed by another component in the inhaler device 100.

The processing starts with the step 402 and the controller 106 detects or estimates the capacities of the respective elements of the plurality of elements of the inhaler device 100. The meanings of the terms "element" and "capacity" have already been explained in relation to the first embodiment. In this embodiment, the inhaler device 100 includes a plurality of elements. For example, the inhaler device 100A shown in FIG. 1A has as its elements the first member (for example, battery accommodation unit) 102 (or the battery 110) and the second member (for example, cartridge) 104 (or the reservoir 116). The inhaler device 100B shown in FIG. 1B has the third member (for example, capsule) 126 (or flavor source 128) as its element in addition to these two elements. As has already been described in relation to the first embodiment, the capacities of the elements can be detected or estimated by various methods. The capacity of at least one element of the plurality of elements (for example, the battery 110 of the first member 102) can be detected or estimated by a method different than that for the capacity of another element among the plurality of elements (for example, the third member (capsule) 126). Also, the capacity of at least one element of the plurality of elements can be detected or estimated by the same method as that for at least one different element among the plurality of elements. For example, both of the capacity of the capsule 126 and the capacity of the cartridge 104 may be detected or estimated on the basis of the cumulative energization time for the atomizing part 118 or a cumulative amount of power. Also, both of the capacity of the battery 110 and the capacity of the cartridge 104 may be detected or estimated on the basis of a cumulative current value.

The processing proceeds to the step 404. In the step 404, the controller 106 determines whether or not the predefined condition specified for the element is satisfied which includes the requirement that the capacity of the element detected or estimated in the step 402 is equal to or lower than the threshold specified for the element. The threshold and the predefined condition specified for each element may be stored in the memory 114 in association with the element. The controller 106 may acquire the threshold and the predefined condition from the memory 114. Regarding at least one element of the plurality of elements, the above-described predefined condition may include other requirements in addition to the requirement that the capacity of the element is equal to or lower than the threshold. For example, regarding at least one element, the predefined condition may further include the requirement that the predefined variable detected in the inhaler device 100 satisfies a predetermined requirement. In one example, if the sensor 112 is a pressure sensor that detects a pressure or a flow sensor that detects a flow rate in the air intake flow path 120 and/or the aerosol flow path 121, the predefined variable may be pressure or flow rate. In another example, if the inhaler device 100 includes a button (not shown) for driving, then the predefined variable may be stress, current value, or the like indicative of the fact that the button has been pressed.

If the predefined condition is not satisfied ("No" in the step 404), the processing goes back to the stage before the step 402. If the predefined condition is satisfied ("Yes" in the step 404), the processing proceeds to the step 406. In the step 406, the controller 106 performs a predetermined notification to the user (that is, the inhaler of the inhaler device 100). For example, the controller 106 causes the notifying part 108 to function in a predetermined manner. In one example, if the predefined condition specified for the first member 102 (or the battery 110) is satisfied, the controller 106 may cause the notifying part 108 to function in a particular manner. In another example, if the predefined condition specified for the second member 104 (or the reservoir 116) is satisfied, the controller 106 may cause the notifying part 108 to function in another manner. Further, in another example, if the predefined condition specified for the third member 126 (or flavor source 128) is satisfied, the controller 106 may cause the notifying part 108 to function in still another manner. The notification of the step 406 is performed in order to notify the user that replacement, filling, charging, etc. of elements (which is hereinafter referred to as "replacement, etc." as required) is necessary.

The predefined condition determined in the step 402 becomes stricter for one of the plurality of elements that the inhaler device 100 includes if the work for returning the capacity of the one element at issue to the state where it has the capacity needed to continuously generate the aerosol or aerosol imparted with flavor (which may be hereinafter generically referred to as "aerosol") should be more frequently performed. In one example, the predefined condition will be less likely to be satisfied for one element on which the work should be more frequently performed among the elements. In another example, the predefined condition includes more requirements for one of the elements on which the work should be more frequently performed. For example, if the inhaler device has the features of the inhaler device 100A shown in FIG. 1A and the frequency of replacement of the second member 104 (or the reservoir 116) is higher than the frequency of charging of the battery 110 in the first member 102, then the predefined condition specified for the second member 104 is stricter than the predefined condition specified for the battery 110 of the first member 102. Also, if the inhaler device has the features of the inhaler device 100B shown in FIG. 1B and frequency of replacement of the third member 126 (or flavor source 128) is highest and the frequency of replacement of the second member 104 is second highest, and the frequency of charging of the battery 110 of the first member 102 is lowest, then the predefined condition specified for the third member 126 may be strictest, the predefined condition specified for the second member 104 may be second strictest, and the predefined condition specified for the battery 110 of the first member 102 may be most moderate. Further, in the configuration of FIG. 1B, the predefined condition may be specified only for the battery 110 of the first member 102 and the third member 126 while no condition may be specified for the second member 104. In this case, in the step 402, only the capacity of the battery 110 and the capacity of the third member 126 are detected or estimated and, in the step 404, only the predefined condition specified for the battery 110 and the third member 126 is determined. If the frequency of replacement of the third member 126 is higher than the frequency of charging of the battery 110 of the first member 102, the condition specified for the third member 126 is stricter than the condition specified for the battery 110.

In this embodiment, the inhaler device 100 may include a plurality of identical elements or a plurality of elements of the same kind. For example, the inhaler device 100B shown in FIG. 1B may be configured to be capable of accommodating a plurality of the third members (for example, first and second capsules) 126 (or first and second flavor sources). In this example, the first and second capsules may contain the flavor sources of the same kind having the same maximum capacity, may contain the flavor sources of the same kind having different maximum capacities, may contain the flavor sources of different kinds having the same maximum capacity, or may contain the flavor sources of different kinds having different maximum capacities. In this example, in the step 402, the capacity of the first capsule and the capacity of the second capsule may be detected or estimated by the same method. If the frequency of replacement of the first capsule is higher than the frequency of replacement of the second capsule, then the predefined condition specified for the first capsule which is determined in the step 404 is stricter than the predefined condition specified for the second capsule. It will also be appreciated that the processing of the embodiment of FIG. 4 can be implemented when the inhaler device 100 includes a plurality of batteries 110 and/or a plurality of the second members (for example, cartridge) 104 (or the reservoir 116).

Figure 5:
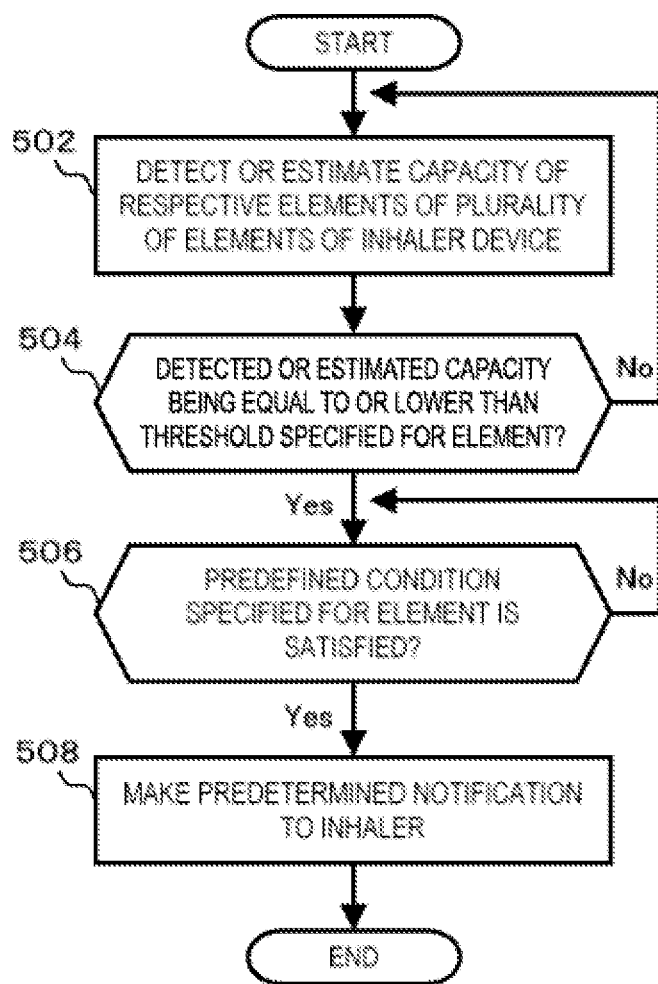
FIG. 5 is a flowchart showing another basic operation of the inhaler device according to the second embodiment of the present disclosure.

FIG. 5 is a flowchart that shows another basic operation of the inhaler device 100 according to the second embodiment of the present disclosure.

The processing starts with the step 502. The process at the step 502 is the same as the process at the step 402.

The processing proceeds to the step 504 and the controller 106 determines whether or not the capacity of the element detected or estimated at the step 502 is equal to or lower than the threshold set for this element. If the capacity is not equal to or lower than the threshold ("No" in the step 504), the processing goes back to the stage before the step 502. If the capacity is equal to or lower than the threshold ("Yes" in the step 504), the processing proceeds to the step 506.

In the step 506, the controller 106 determines whether or not the predefined condition specified for the element whose capacity has been determined in the step 504 as being equal to or lower than the threshold is satisfied. Since the "predefined condition" has already been explained in relation to FIG. 4, explanations thereof will not be repeated here. If the predefined condition is not satisfied ("No" in the step 506), the processing goes back to the stage before the step 506. If the predefined condition is satisfied ("Yes" in the step 506), the processing proceeds to the step 508. The process at the step 508 is the same as the process at the step 406.

In the embodiment shown in FIG. 5 as well, in the same manner as in FIG. 4, the predefined condition determined at the step 506 becomes stricter for one of the plurality of elements that the inhaler device 100 includes if the work for returning the capacity of the one element at issue to the state where it has the capacity needed to continuously generate the aerosols should be more frequently performed. Also, the inhaler device 100 may include a plurality of identical elements or a plurality of elements of the same kind.

FIG. 6 is a flowchart that shows in detail an example of operation of the inhaler device 100 according to this embodiment. In the following description, the controller 106 will be described as executing all the steps shown in FIG. 6. However, it should be noted that some steps of FIG. 6 may be performed by other components in the inhaler device 100. Here, the inhaler device has the features of the inhaler device 100B shown in FIG. 1B and the first member (for example, battery accommodation unit) 102 (or the battery 110), the second member (for example, cartridge) 104 (or the reservoir 116), and the third member (for example, capsule) 126 (or flavor source 128) of the inhaler device 100B are described as being the "element" in FIGS. 4 and 5. As has already been described, it should be noted that there may be a plurality of identical elements or similar elements. Note that in the embodiment of FIG. 6, the determinations regarding the threshold and the predefined condition are performed only for the first member 102 (or the battery 110) and the third member (capsule) 126 (or flavor source 128) while such determinations are not performed on the second member (cartridge) 104 (for example, the reservoir 116). Specifically, the embodiment of FIG. 6 may encompass a case where the second member 104 does not satisfy the threshold or the predefined condition and a case where the threshold and the predefined condition are not specified for the second member 104. Here, out of the battery 110 and the capsule 126 which are the elements of the inhaler device 100B, the work for returning the state where the element has a capacity needed to continuously generate aerosols is more frequently performed on the capsule 126. In one example, the battery 110 may be charged at least once while the capsule 126 is replaced for ten times.

The processing starts with the step 602. In the step 602, the controller 106 determines whether or not start of puffing of the inhaler device 100 by the user has been detected. As an example, if the sensor 112 includes a pressure sensor or a flow sensor, the controller 106 may determine that the puffing has been started when the pressure or flow rate acquired from the sensor 112 exceeded a predefined value. The controller 106 may also determine that the puffing has been started when the duration in which the pressure or flow rate is detected by the sensor 112 exceeds a predetermined duration. In another example, the controller 106 may determine that the puffing has been started when the inhaler device 100 includes a start button and the button has been pressed. If the start of the puffing is not detected ("No" in the step 602), the processing goes back to the stage before the step 602. If the start of the puffing has been detected ("Yes" in the step 602), the processing proceeds to the step 604.

The step 604 is an example of the step 404 of FIG. 4 or the step 504 (and the step 506) of FIG. 5 regarding the battery 110 as an element of the inhaler device 100B. In the step 604, the controller 106 determines whether or not the voltage of the battery 110 is larger than the threshold (discharge cutoff voltage (for example, 3.2 V), etc.). If the voltage of the battery 110 is equal to or lower than the discharge cutoff voltage ("No" in the step 604), the processing proceeds to the step 606. The step 606 is an example of the step 406 of FIG. 4 or the step 508 of FIG. 5 regarding the battery 110. In the step 606, the controller 106 causes the notifying part 108 to function in the first manner. In one example, if the notifying part 108 includes an LED, the first manner may include causing the LED to blink in red for 5.4 seconds. After that, the processing is ended. On the other hand, if the voltage of the battery 110 is larger than the discharge cutoff voltage ("Yes" in the step 604), the processing proceeds to the step 608.

The processing from the step 608 to the step 612 is the same as the processing from the step 308 to the step 312 of FIG. 3 and explanations thereof will not be repeated here.

The processing proceeds to the step 614 and the controller 106 causes the notifying part 108 to function in the second manner. The second manner is a manner of operation of the notifying part 108 when the user is performing normal suction using the inhaler device 100B. In one example, if the notifying part 108 includes an LED, in the step 614, the controller 106 may cause the LED to be lit in blue constantly.

The processing from the step 616 to the step 628 is the same as the processing from the step 316 to the step 328 of FIG. 3 and explanations thereof will not be repeated here.

The steps 630 to 634 are an example of the step 404 of FIG. 4 or the step 504 and 506 of FIG. 5 regarding the third member (capsule) 126 as an element of the inhaler device 100B. In the step 630, the controller 106 determines whether or not the cumulative time $T_A$ is longer than the predetermined threshold time. The threshold time can be defined as the cumulative time of the inhaling on the inhaler device 100B at which it is estimated that the capacity (in this example, the residual amount of the flavoring ingredients contained in the flavor source 128) of the capsule 126 is lower than the value needed to generate aerosol imparted with sufficient flavor. The threshold time may be stored in advance in the memory 114, etc. If $T_A$ is equal to or shorter than the threshold time ("No" in the step 630), then it follows that the capacity of the capsule 126 has been determined as being larger than the threshold specified for the capsule 126, and the processing goes back to the stage before the step 602. If $T_A$ is longer than the threshold time ("Yes" in the step 630), then it follows that the capacity of the capsule 126 has been determined as being equal to or lower than the threshold specified for the capsule 126, and the processing proceeds to the step 632.

In the step 632, the controller 106 determines whether or not the start of the puffing has been detected. In one example, if the sensor 112 includes a pressure sensor or a flow sensor, the controller 106 may determine that the puffing has been started when the pressure or flow rate acquired from the sensor 112 has an absolute value exceeding a predefined value.

If the start of the puffing is not detected ("No" in the step 632), the processing goes back to the stage before the step 632. Specifically, the controller 106 waits for the start of the puffing being detected. If the start of the puffing has been detected ("Yes" in the step 632), the processing proceeds to the step 634.

In the step 634, the controller 106 determines whether or not the puffing continues for a predetermined period of time (for example, 1.0 second). The predetermined period of time may be stored in the memory 114. If the puffing does not continue for a predetermined period of time ("No" in the step 634), the processing goes back to the stage before the step 632. If the puffing has continued for the predetermined period of time ("Yes" in the step 634), the processing proceeds to the step 636. By performing the step 634, it is made possible to prevent the subsequent processes from being performed even when it has been erroneously determined that the start of the puffing was detected in the step 632 due to occurrence of background noise.

Both of the processes at the steps 632 and 634 may be performed or only one of them may be performed.

In the step 636, the controller 106 prohibits energization of the atomizing part 118. Note that the process at the step 636 may be performed between the step 630 and the step 632.

The processing proceeds to the step 638. The step 638 is an example of the step 406 of FIG. 4 or the step 508 of FIG. 5 regarding the capsule 126. In the step 638, the controller 106 causes the notifying part 108 to function in the third manner. In one example, if the notifying part 108 includes an LED, the third manner may include causing the LED to blink in blue. The controller 106 may cause the notifying part 108 to function for a relatively long time (for example, 40 seconds) so that the user can notice the fact that the capacity of the capsule 126 is insufficient.

The processing from the step 640 to the step 644 is the same as the processing from the step 340 to the step 344 of FIG. 3 and explanations thereof will not be repeated here.

The condition that should be satisfied for causing the notifying part 108 to function in the third manner regarding the capsule 126 in the step 638 is stricter than the condition that should be satisfied for causing the notifying part 108 to function in the first manner regarding the battery 110 in the step 606. Since the condition for the notifying part 108 to operate is stricter for an element on which the replacement, etc. is more frequently performed, it is made easier to prevent malfunction of the notifying part 108. Accordingly, it is made possible to reduce the possibility that the user overlooks the operation of the notifying part 108 urging the replacement regarding an element on which the replacement, etc. is frequently performed.

The condition that should be satisfied for causing the notifying part 108 to function in the first manner regarding the battery 110 in the step 606 includes one requirement that the voltage of the battery 110 is equal to or lower than the discharge cutoff voltage. In contrast, the condition that should be satisfied for causing the notifying part 108 to function in the third manner regarding the capsule 126 in the step 638 includes two requirements, i.e., that (i) $T_A$ is longer than the threshold time and that (ii) the start of the puffing has been detected, and may further include another requirement that (iii) the puffing continued for a predetermined period of time. Specifically, in this embodiment, the condition that is determined regarding the capsule 126 in relation to the processing of FIG. 4 or 5 includes more requirements than the condition that is determined regarding the battery 110 in relation to this processing. In other words, the above-described condition may include more requirements for an element on which the work for returning the element at issue to the state where it has the capacity needed for continuously generating the aerosol is more frequently performed among the plurality of elements of the inhaler device 100B. Since the condition for the notifying part 108 to operate includes more requirements for an element on which the replacement, etc. is performed with higher frequency, malfunction of the notifying part 108 is readily prevented. Accordingly, it is made possible to reduce the possibility that the user overlooks the operation of the notifying part 108 urging the replacement regarding an element on which the replacement, etc. is frequently performed.

Figure 6:
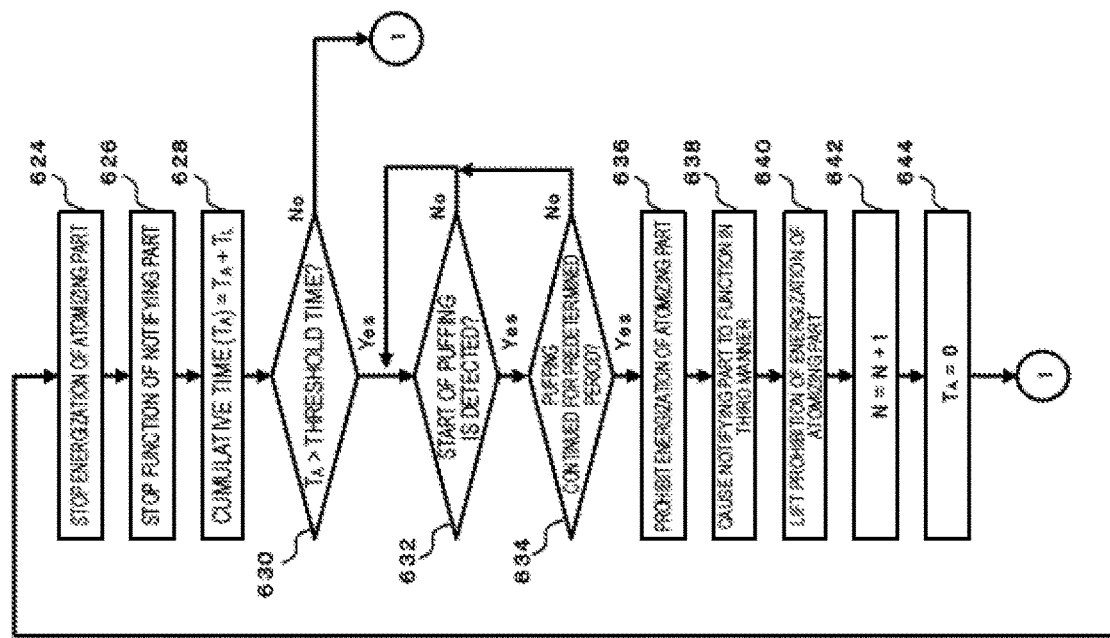
FIG. 6 is a flowchart showing, in detail, an example of the operation of the inhaler device according to the second embodiment of the present disclosure.
Figure 6:
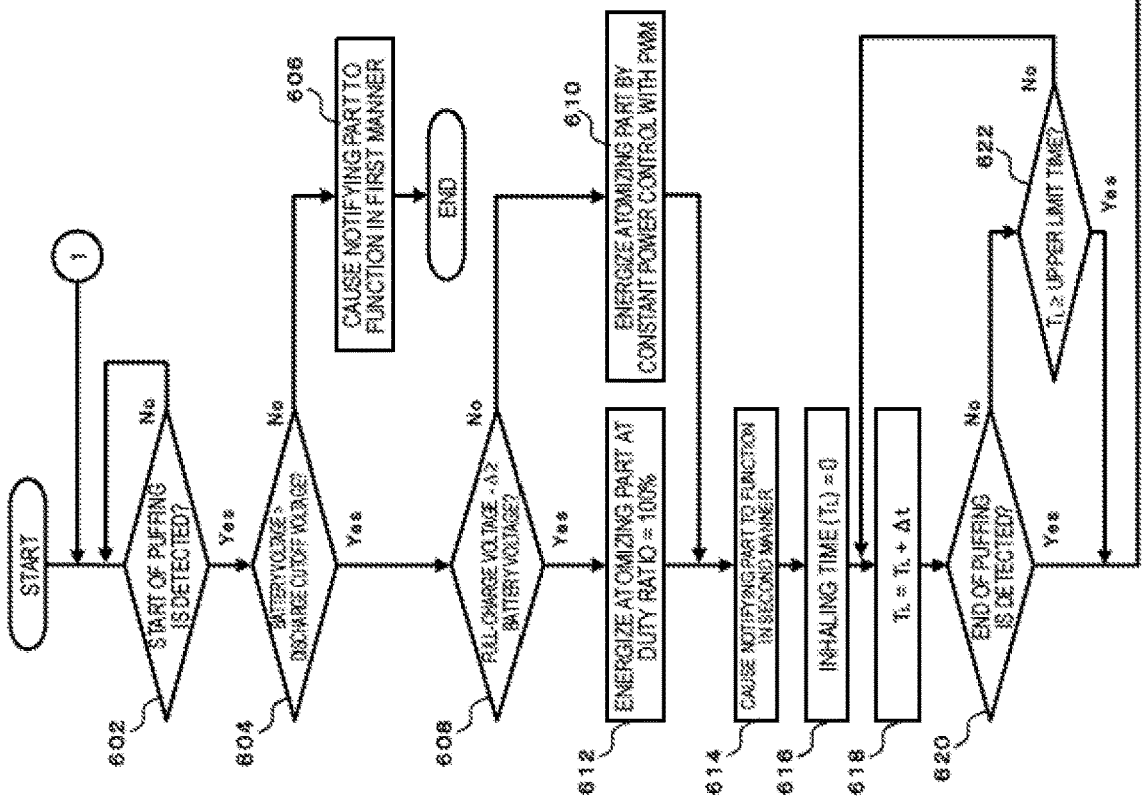

Note that the controller 106 may not perform a part of the steps shown in FIG. 6 or the order of the part of the steps may be modified. For example, whether or not the start of the puffing has been detected may not be determined in the step 602 before the notifying part is made to function in the first manner in the step 606. In other words, the controller may perform the step 602 after the controller has determined in the step 604 whether or not the voltage of the battery 110 is equal to or lower than the discharge cutoff voltage. In this embodiment, it will be clearly appreciated that the condition that should be satisfied to cause the notifying part 108 to function in the first manner in relation to the battery 110 at the step 606 includes only one requirement that the voltage of the battery 110 is equal to or lower than the discharge cutoff voltage.

Also, the controller 106 may always continue the determination at the step 604 in the processes at and after the step 602. That is, in the course of performing the steps 608 to 644, when the voltage of the battery 110 that the controller 106 detects becomes equal to or lower than the discharge cutoff voltage ("Yes" in the step 604), then the step 606 is performed as interrupt processing and the controller 106 causes the notifying part 108 to function in the first manner. In this embodiment, the condition that should be satisfied for causing the notifying part 108 to function in the first manner in relation to the battery 110 at the step 606 includes the requirement of whether or not the detection of puffing in the step 602 has been started. However, this requirement is a relatively moderate one only requiring that the step 604 should be satisfied at either of the steps after "Yes" was obtained by the determination at the step 602. In contrast, the condition that should be satisfied to cause the notifying part 108 to function in the third manner regarding the capsule 126 in the step 638 includes a relatively strict requirement that the controller 106 obtained "Yes" by its determination in relation to the steps 632 and 634 immediately after the controller 106 at the step 630 determined that the cumulative time $T_A$ is longer than the predetermined threshold time ("Yes" in the step 630). In other words, the step 606 is a process that can be performed during the aerosol generation, whereas the step 638 is a process that cannot be satisfied during the aerosol generation.

Alternatively, the controller 106 may perform the determination of the step 604 only immediately after the determination resulted in "Yes" in the step 602. In this embodiment, the condition that should be satisfied for causing the notifying part 108 to function in the first manner regarding the battery 110 in the step 606 includes the requirement that the start of the puffing has been detected in addition to the requirement that the voltage of the battery 110 is equal to or lower than the discharge cutoff voltage. However, the condition that should be satisfied for causing the notifying part 108 to function in the first manner regarding the battery 110 in the step 606 does not include the requirement that (iii) the puffing continued for a predetermined period of time, which is included in the condition that should be satisfied for causing the notifying part 108 to function in the third manner regarding the capsule 126 in the step 638. Hence, in any of these embodiments, the condition that should be determined regarding the capsule 126 in relation to the processing of FIG. 4 or FIG. 5 includes more requirements than the condition that should be determined regarding the battery 110 in relation to this processing.

In relation to the step 632, the controller 106 is configured to acquire a request for generation of the aerosol. For example, the controller 106 may determine that the request for the generation of the aerosol has been made when the sensor 112 has detected a pressure that is larger than a predetermined value. In another example, if the sensor 112 sends the request for the generation of the aerosol to the controller 106 in response to the pressure larger than the predetermined value having been detected, then the controller 106 may determine that the request has been made. Detection of the above-mentioned request may correspond to the detection of the start of the puffing in the step 632. Accordingly, out of the battery 110 and the capsule 126, the condition that should be determined regarding the capsule 126 for which the above-described frequency is highest may include the detection of the above-described request. By virtue of this feature, the element having the highest frequency of the replacement, etc. includes the puffing detection as the condition for causing the notifying part 108 to function. Accordingly, since the notifying part 108 operates when the user clearly wants to perform inhaling, it is made possible to more effectively reduce the possibility that the user overlooks the operation of the notifying part 108.

The condition when it is determined in the step 632 that the start of the puffing has been detected may be stricter than the condition when it is determined in the step 602 that the start of the puffing has been detected. For example, the predefined value used in the determination in the step 632 may be greater than the predefined value used in the determination in the step 602. Also, the duration used in the determination in the step 632 may be longer than the duration used in the determination in the step 602.

In relation to the steps 606 and 638, the controller 106 may be configured to cause the notifying part 108 to function for a longer period of time when the condition for an element among a plurality of elements is satisfied if this element has the higher frequency described above among the plurality of elements. Specifically, since the above-describe frequency becomes higher for the capsule 126 than the battery 110, the period of time in which the notifying part 108 functions in the step 638 may be longer than the period of time in which the notifying part 108 functions in the step 606. By virtue of this feature, in relation to an element on which replacement, etc. is frequently performed, it is made possible to more effectively reduce the possibility that the user overlooks the operation of the notifying part 108.

If the notifying part 108 includes a light emitting element such as an LED, the controller 106 may specify different light emission colors for respective elements. For example, the controller 106 may set the light emission color of the light emitting element for the battery 110 to red and may set the light emission color of the light emitting element for the capsule 126 to blue. The controller 106 may specify the light emission colors of the light emitting element for the respective elements on the basis of the above-described frequency associated with the respective elements of the plurality of elements. By virtue of this feature, the user will be able to more easily recognize which element the replacement, etc. should be performed on.

For example, the controller 106 may select the light emission color of the light emitting element from colder colors for an element having the higher frequency among the plurality of elements. By selecting the frequently lit color from cold colors, it is made possible to urge the user to perform the replacement work in sense of usual use without causing the user to be excessively on alert.

Also, the controller 106 may select the light emission color of the light emitting element from warmer colors for an element having the lower frequency among the plurality of elements. In a broader concept, the controller 106 may select the light emission color of the light emitting element from the colors having a shorter wavelength for an element having the higher frequency among the plurality of elements and may select the light emission color of the light emitting element from the colors having a longer wavelength for an element having the lower frequency. By selecting the light emission color of the light emitting element from warm colors regarding the element having low frequency of replacement, etc., it is made possible to strongly attract the attention of the user when the time of replacement comes for an element replacement of which is only rarely necessitated.

The controller 106 may also be configured to control the light emitting element such that the light emission color of the light emitting element in the case where the condition is satisfied regarding the element having the highest frequency among the plurality of elements becomes identical with the light emission color of the light emitting element during the generation of the aerosol. Specifically, in the example of FIG. 6, the controller 106 may also set the light emission color of the light emitting element in the normal operation of the step 614 to blue and may likewise set to blue the light emission color of the light emitting element in the step 638 associated with the capsule 126 which have the highest frequency of the battery 110 and the capsule 126. By virtue of this feature, it is made possible to allow the user to understand the fact that the replacement, etc. should be performed on the element having the highest frequency of replacement, etc. (that is, the frequency of the notification to the user) without impairing the user experience.

The controller 106 may be configured to suspend the function of the notifying part 108 when at least one element of the plurality of elements has been removed. In the example of FIG. 6, if the second member 104 and the third member 126 are removable, the controller 106 may suspend the function of the notifying part 108 when either or both of these members have been removed.

Figure 7:
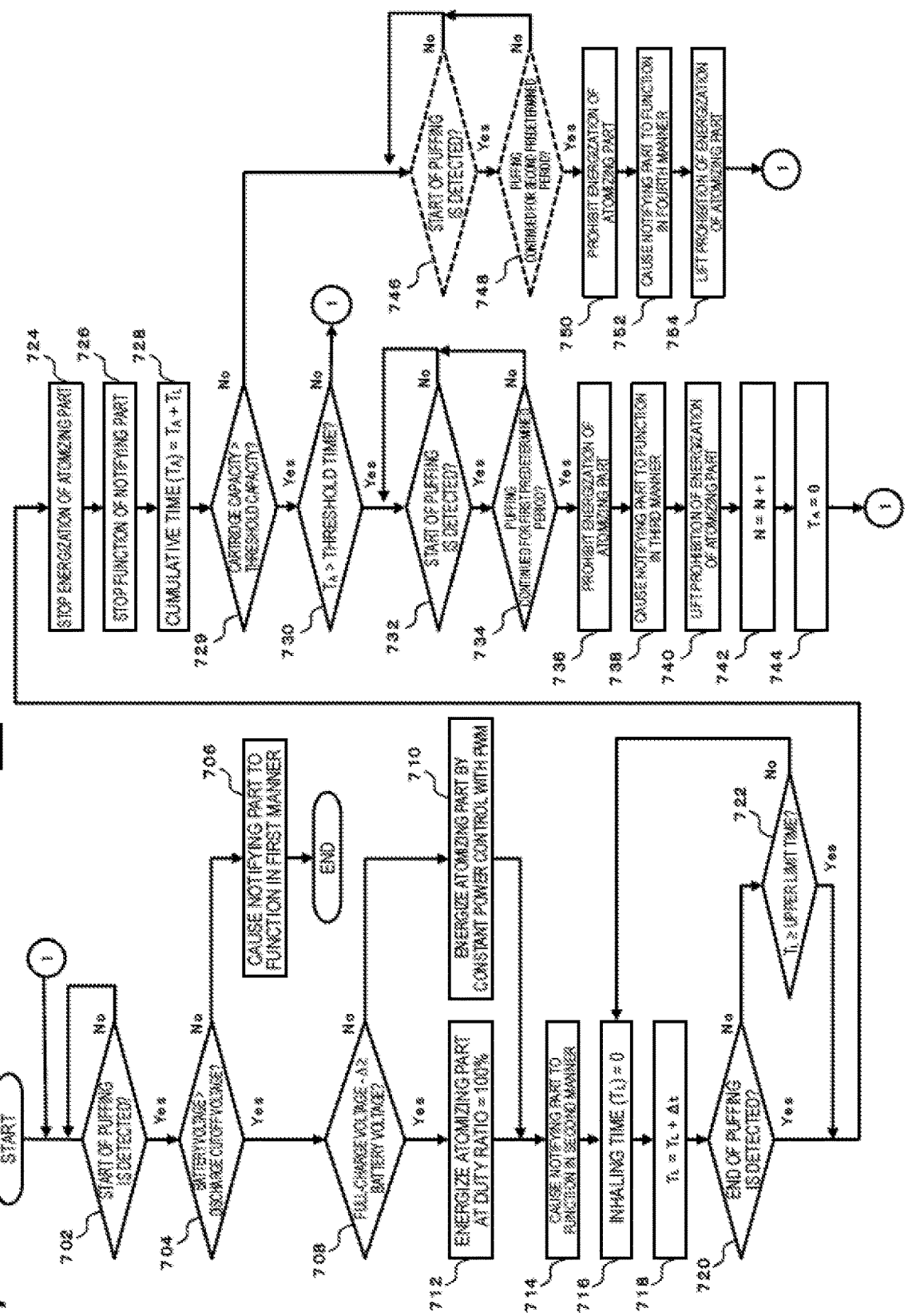
FIG. 7 is a flowchart showing, in detail, an example of the operation of the inhaler device according to the second embodiment of the present disclosure.

FIG. 7 is a flowchart that shows in detail an example of the operation of the inhaler device 100 according to this embodiment. In the same manner as in FIG. 6, explanations will be provided on the assumption that the inhaler device has the features of the inhaler device 100B shown in FIG. 1B and the battery accommodation unit 102 (or the battery 110), the cartridge 104 (or the reservoir 116) and the capsule 126 (or flavor source 128) are the "elements" in FIGS. 4 and 5. Not that, in the embodiment of FIG. 7, it is assumed that the determinations regarding the thresholds and the predefined conditions are made on the battery 110, the cartridge 104, and the capsule 126. Here, it is assumed that, out of the battery 110, cartridge 104, and the capsule 126 which are the elements of the inhaler device 100B, the frequency at which the work for returning an element to a state where it has a capacity necessary for continuously generating the aerosol is performed is highest for the capsule 126, second highest for the cartridge 104, and lowest for the battery 110. In one example, the cartridge 104 may be replaced twice and the battery 110 may be charged once while the capsule is replaced for ten times.

The processing starts with the step 702. The processing from the step 702 to the step 728 is the same as the processing from the step 602 to the step 628 of FIG. 6 and explanations thereof will not be repeated here. In the same manner as in the step 606 of FIG. 6, in the step 706, the controller 106 causes the notifying part 108 to function in the first manner. In one example, if the notifying part 108 includes an LED, the first manner may include causing the LED to blink in red for 5.4 seconds.

The steps 729, 746, and 748 are examples of the step 404 of FIG. 4 or the steps 504 and 506 of FIG. 5 regarding the cartridge 104 as one element of the inhaler device 100B. The steps 729 to 734 are examples of the step 404 of FIG. 4 or the steps 504 and 506 of FIG. 5 regarding the capsule 126 as one element of the inhaler device 100B.

In the step 729, the controller 106 determines whether or not the capacity of the cartridge 104 is larger than a predetermined threshold capacity. If the capacity of the cartridge 104 is larger than the threshold capacity ("Yes" in the step 729), the processing proceeds to the step 730. The processing from the step 730 to the step 744 is the same as the processing from the step 630 to the step 644 of FIG. 6 and explanations thereof will not be repeated here. Note that, in the step 734, the controller 106 determines whether or not the puffing has continued for the first predetermined period of time (for example, 1.0 second). Also, in the step 738, the controller 106 causes the notifying part 108 to function in the third manner. In one example, if the notifying part 108 includes an LED, the third manner may include causing the LED to blink in blue. The controller 106 may cause the notifying part 108 to function for a relatively long time (for example, 40 seconds) so that the user can notice the fact that the capacity of the capsule 126 is insufficient.

In the step 729, if the capacity of the cartridge 104 is equal to or lower than the threshold capacity ("No" in the step 729), the processing proceeds to the step 746. In the step 746, the controller 106 determines whether or not the start of the puffing has been detected. In one example, if the sensor 112 includes a pressure sensor or a flow sensor, the controller 106 may determine that the puffing has been started when the pressure or flow rate acquired from the sensor 112 has an absolute value exceeding a predefined value. The controller 106 may also determine that the puffing has been started when the duration in which the pressure or flow rate is detected by the sensor 112 exceeds a predefined duration.

When start of puff is not detected ("No" in step 746), the process returns to before step 746. When start of puff is detected ("Yes" in step 746), the process proceeds to step 748.

In step 748, the controller 106 determines whether or not puff continues for a second predetermined time (for example, 0.5 seconds). The second predetermined time may be stored in the memory 114. When puff does not continue for the second predetermined time ("No" in step 748), the process returns to before step 746. When puff continues for the second predetermined time ("Yes" in step 748), the process proceeds to step 750. The processes in step 746 and 748 may be both executed, or only one of the processes may be executed. Alternatively, the processes in step 746 and 748 may be omitted.

In step 750, the controller 106 prohibits energization to the atomizing part 118. Note that the process in step 750 may be performed between step 729 and step 746.

The process proceeds to step 752, and the controller 106 causes the notifying part 108 to function in the fourth manner. In one example, when the notifying part 108 includes LED, the third manner may include flashing the LED in green color. The controller 106 may cause the notifying part 108 to function for a somewhat long time (for example, 20 seconds) such that the user notices that the capacity of the cartridge 104 is insufficient.

A condition that should be satisfied to cause the notifying part 108 to function in the first manner concerning the battery 110 in step 706 includes one requirement that the voltage of the battery 110 is equal to or lower than a discharge cutoff voltage. In contrast to this, a condition that should be satisfied to cause the notifying part 108 to function in the fourth manner concerning the cartridge 104 in step 752 includes two requirements that (i) the capacity of the cartridge 104 is equal to or lower than a threshold capacity, and (ii) start of puff is detected, and further may include another requirement that (iii) puff continues for a predetermined time. Further, a condition that should be satisfied to cause the notifying part 108 to function in the third manner concerning the capsule 126 in step 738 includes three requirements that (i) the capacity of the cartridge 104 is larger than a threshold capacity, (ii) $T_A$ is larger than a threshold time, and (iii) start of puff is detected, and further may include another requirement that (iv) puff continues for a predetermined time. That is, in the present embodiment, the condition that is determined concerning the capsule 126 in relation to the process in FIG. 4 or FIG. 5 includes the largest number of requirements, the condition that is determined concerning the cartridge 104 in relation to the process in FIG. 4 of FIG. 5 includes the second largest number of requirements, and the condition that is determined concerning the battery 110 in relation to the process in FIG. 4 or FIG. 5 includes the smallest number of requirements. In other words, the conditions that are set to the elements higher in frequency with which the operation for returning the elements into a state having a necessary capacity to generate aerosol continuously, among the plurality of elements of the inhaler device 100B may include a larger number of requirements.

Note that the controller 106 may omit some of the steps illustrated in FIG. 7, or may change an order of some of the steps. For example, whether or not start of puff is detected does not have to be determined in step 702 before the notifying part is caused to function in the first mode in step 706. In other words, the controller may execute step 702 after the controller determines whether or not the voltage of the battery 110 is equal to or lower than the discharge cutoff voltage in step 704. In the present embodiment, it is apparent that the condition that should be satisfied to cause the notifying part 108 to function in the first mode concerning the battery 110 in step 706 includes only the one requirement that the voltage of the battery 110 is equal to or lower than the discharge cutoff voltage.

Further, in the processes after step 702, the controller 106 may always continue performing determination in step 704. That is, when the voltage of the battery 110 which is detected by the controller 106 becomes equal to or lower than the discharge cutoff voltage ("yes" in step 704) in the process of executing steps 708 to 754, the controller executes step 706 as interrupt processing, and the controller 106 causes the notifying part 108 to function in the first manner. In the present embodiment, the condition which should be satisfied to cause the notifying part 108 to function in the first manner concerning the battery 110 in step 706 includes the requirement of whether or not detection of puff in step 702 is started. However, the requirement is relatively loose so that step 704 only has to be satisfied in any one of the steps after it is determined as "yes" in step 702. In contrast to this, the condition that should be satisfied to cause the notifying part 108 to function in the third manner concerning the capsule 126 in step 738 includes a relatively strict requirement that the controller 106 make determination of "yes" concerning step 732 and step 734 immediately after the controller 106 determines that an cumulative time $T_A$ is larger than a predetermined threshold time in step 730 ("yes" in step 730). Likewise, the condition that should be satisfied to cause the notifying part 108 to function in the fourth manner concerning the cartridge 104 in step 752 includes a relatively strict requirement that the controller 106 makes determination of "yes" concerning step 746 and step 748 immediately after the controller 106 determines that the cartridge capacity is less than the predetermined threshold capacity in step 729 ("No" in step 729). In other words, step 706 is the process that can be also executed during generation of aerosol, whereas step 738 and step 752 are the processes that cannot be satisfied during generation of aerosol.

Further, the controller 106 may perform determination of step 704 only immediately after it is determined as "yes" in step 740. In the present embodiment, the condition that should be satisfied to cause the notifying part 108 to function in the first manner concerning the battery 110 in step 706 includes the requirement that start of puff is detected in addition to the requirement that the voltage of the battery 110 is equal to or lower than the discharge cutoff voltage. However, the condition that should be satisfied to cause the notifying part 108 to function in the first manner concerning the battery 110 in step 706 does not include the requirement that (iii) puff continues for the predetermined time, which is included in the condition which should be satisfied to cause the notifying part 108 to function in the third manner concerning the capsule 126 in step 738, or the condition that should be satisfied to cause the notifying part to function in the fourth manner concerning the cartridge 104 in step 752. Therefore, in any of the embodiments, the conditions that are determined concerning the capsule 126 and the cartridge 104 include a larger number of requirements than the condition that is determined concerning the battery 110 in relation to the process.

The requirement for start of puff being determined as detected in step 732 may be stricter than the requirement for start of puff being determined as detected in step 746. In one example, when the sensor 112 includes a pressure sensor or a flow rate sensor, the controller 106 may determine that puff is started when the pressure acquired from the sensor 112 exceeds a first predetermined value, in step 732. On the other hand, in step 746, the controller 106 may determine that puff is started when the pressure acquired from the sensor 112 exceeds a second predetermined value that is smaller than the first predetermined value. Further, the first predetermined time (for example, 1.0 second) that is used in determination in step 734 is longer than the second predetermined time (for example, 0.5 seconds) that is used in determination in step 748. That is, in the present embodiment, the condition that is determined concerning the capsule 126 in relation to the process in FIG. 4 or FIG. 5 has a lower possibility of being satisfied than the condition that is determined concerning the cartridge 104 in relation to the process. In other words, the condition has a lower possibility of being satisfied, which is set to the element higher in frequency with which the operation for returning the element into the state having the capacity necessary to generate aerosol continuously is performed, among the plurality of elements of the inhaler device 100B. The element higher in frequency of replacement or the like has a lower possibility of the condition for operating the notifying part 108 being satisfied, so that an erroneous operation of the notifying part 108 is easily prevented. Accordingly, the possibility of the user overlooking the operation of the notifying part 108 that urges replacement with respect to the element high in frequency of replacement or the like can be reduced.

In the aforementioned explanation, the second embodiment of the present disclosure is described as the inhaler device having the configuration illustrated in FIG. 1A or FIG. 1B and the method illustrated in any one of FIGS. 4 to 7. However, it is understood that when the present disclosure is executed by a processor, the present disclosure can be carried out by the processor as a program that causes the processor to execute the method illustrated in any one of FIGS. 4 to 7, or a computer-readable storage medium storing the program.

Third Embodiment

Figure 8:
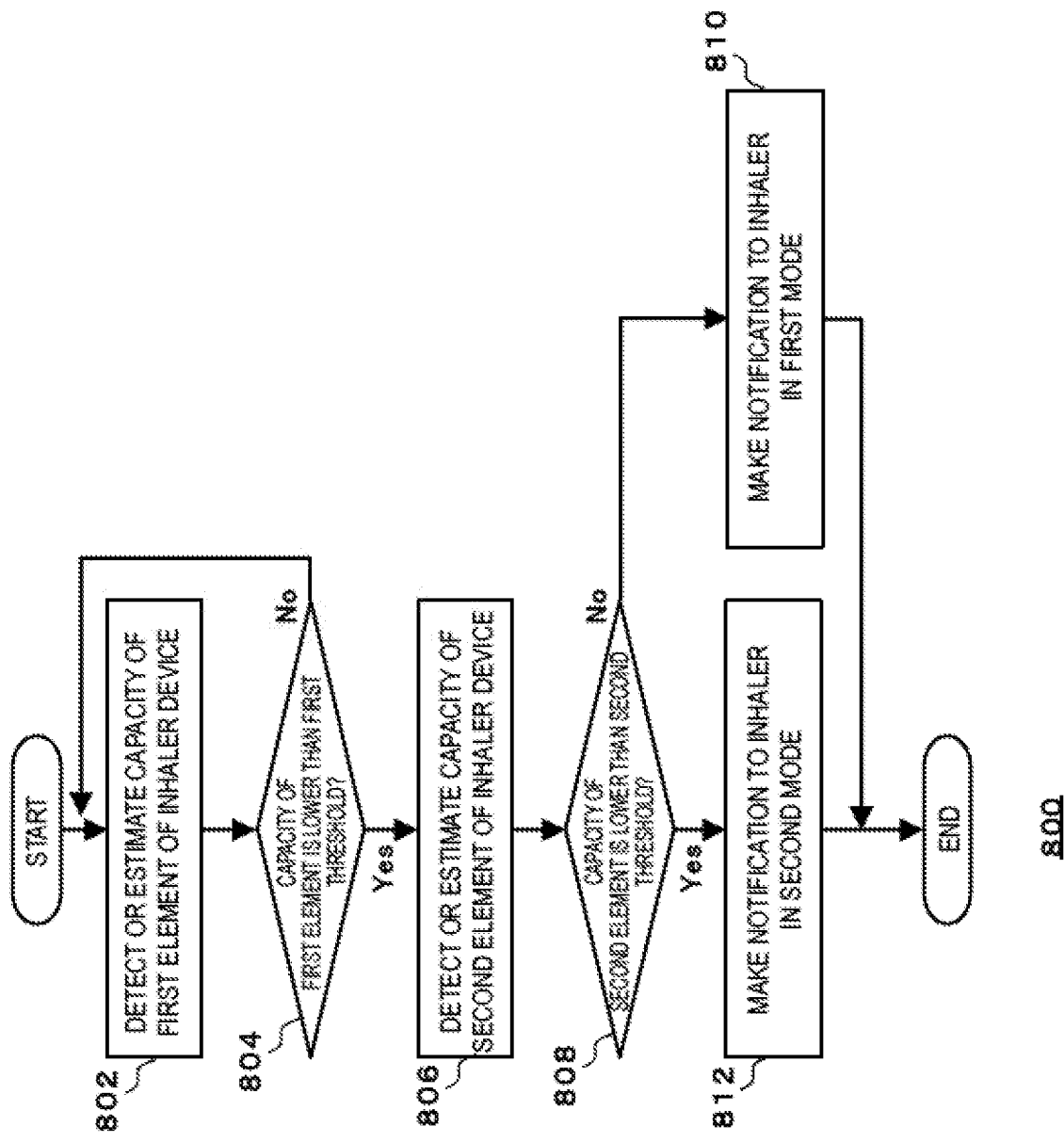
FIG. 8 is a flowchart showing a basic operation of an inhaler device according to a third embodiment of the present disclosure.

FIG. 8 is a flowchart illustrating a basic operation of the inhaler device 100 according to a third embodiment of the present disclosure. Hereinafter, explanation will be made by assuming that the controller 106 executes all steps illustrated in FIG. 8. However, attention should be paid to the fact that some of the steps in FIG. 8 may be executed by other components in the inhaler device 100.

A process is started in step 802, and the controller 106 detects or estimates a capacity of the first element of the inhaler device 100. Meanings of the terms "element" and "capacity" are already described in relation to the first embodiment. In the present embodiment, the inhaler device 100 includes a plurality of elements. For example, the inhaler device 100A illustrated in FIG. 1A has the first member (for example, the battery housing section) 102 (or the battery 110) and the second member (for example, the cartridge) 104 (or the reservoir 116) as the elements. The inhaler device 100B illustrated in FIG. 1B has the third member (for example, the capsule) 126 (or the flavor source 128) as the element in addition to the two elements. The inhaler device 100 also may include a plurality of the same elements or a plurality of the same kinds of elements. For example, the inhaler device 100B illustrated in FIG. 1B may be configured to be able to house a plurality of third members (for example, the first and second capsules) 126. In this example, the first and second capsules may include the same kind of flavor source having the same maximum capacity, may include the same kind of flavor source having different maximum capacities, or may include different kinds of flavor sources having different maximum capacities. Likewise, the inhaler device 100 may include a plurality of cartridges 104 and a plurality of batteries 110 as elements.

Hereinafter, an example in which the inhaler device has the configuration of the inhaler device 100B in FIG. 1B, and includes the battery 110, the cartridge 104 and the capsule 126 as the elements will be described in detail. However, it is apparent to a person skilled in the art that the present embodiment is also applicable to inhaler devices of other configurations such as the inhaler device 100A in FIG. 1A.

The capacities of the elements can be detected or estimated by various methods. In one example, the sensor 112 may be a weight sensor. In this case, the controller 106 detects the weight of the element by using the sensor 112 (for example, the weight of the liquid or the cigarette in a case where the aerosol source included in the reservoir 116 in the cartridge 104 is a liquid or a cigarette), and may determine that the detected weight as the capacity of the element. In another example, the sensor 112 may be able to detect a height of a liquid level (of the aerosol source or the like included in the reservoir 116 in the cartridge 104). In this case, the controller 106 may detect the height of the liquid level of the element by using the sensor 112, and estimate the capacity of the element based on the detected height of the liquid level. In another example, the memory 114 may store the integration value of energization time to the atomizing part 118. In this case, the controller 106 may estimate the capacity of the element (for example, a residual amount of the aerosol source included in the reservoir 116 in the cartridge 104, a residual amount of flavor and taste components of a cigarette, a residual amount of flavor and taste components included in the flavor source 128 in the capsule 126 and the like) based on the integration energizing time which is acquired from the memory 114. In another example, the memory 114 may store the number of times of inhaling ("puff" in the example of an electronic cigarette) which is performed by the user to the inhaler device 100. In this case, the controller 106 may estimate the capacity of the element based on the number of inhaling times acquired from the memory 114. In another example, the memory 114 may store the data concerning the heating history of the atomizing part 118. In this case, the controller 106 may estimate the capacity of the element based on the data acquired from the memory 114. In another example, the memory 114 may store data concerning SOC (State of Charge, a charging state) of the battery 110, the current integration value and/or the voltage. The sensor 112 may detect these values. In this case, the controller 106 can detect or estimate the capacity of the element (in particular, the battery 110) based on these data. In another example, the sensor 112 may have a fitting detecting function (or connection detecting function) of detecting that the capsule 126 and/or the cartridge 104 are or is detached. In this example, the controller 106 may estimate that the capacity of the capsule 126 is zero when the sensor 112 detects that the capsule 126 is detached. The controller 106 may further estimate that the capacity of the cartridge 104 is zero when the sensor 112 detects that the cartridge 104 is detached.

The capacity of at least one element of the plurality of elements can be detected or estimated by the method different from the method of the capacity of at least one other element out of the plurality of elements. Further, the capacity of at least one element of the plurality of elements can be detected or estimated by the same method as the capacity of at least one other element of the plurality of elements. For example, both of the capacity of the capsule 126 and the capacity of the cartridge 104 may be detected or estimated based on the accumulated energization time to the atomizing part 118 or the accumulated power amount. Further, both the capacity of the battery 110 and the capacity of the cartridge 104 may be detected or estimated based on the accumulated current value.

The process proceeds to step 804. In step 804, the controller 106 determines whether or not the capacity of the first element (for example, the capsule 126) that is detected or estimated in step 802 is less than a first threshold. The first threshold may be stored in the memory 114 by being associated with the first element. The controller 106 may acquire the first threshold from the memory 114. As described above, the capacity of the first element can be detected or estimated by various methods. Accordingly, it is understandable that the first threshold can take various formats and values in accordance with the method that is used to detect or estimate the capacity of the first element.

When the capacity of the first element is not less than the first threshold ("No" in step 804), the process returns to before step 802. When the capacity of the first element is less than the first threshold ("Yes" in step 804), the process proceeds to step 806. In step 806, the controller 106 detects or estimates the capacity of the second element (for example, the cartridge 104) of the inhaler device 100.

The process proceeds to step 808. In step 808, the controller 106 determines whether or not the capacity of the second element which is detected or estimated in step S806 is less than the second threshold. As described above, the capacity of the second element can be detected or estimated by various methods. Accordingly, it is understandable that the second threshold can take various forms and values, in accordance with the method that is used to detect or estimate the capacity of the second element.

When the capacity of the second element is not less than the second threshold ("No" in step 808), the process proceeds to step 810. In step 810, the controller 106 performs notification in the first mode to an inhaler (user) of the inhaler device 100. For example, the controller 106 causes the notifying part 108 to function in the first mode. The notifying part 108 may include a light emitting element such as an LED, a display, a speaker, and a vibrator. The notifying part 108 is configured to perform some sort of notification to the user by light emission, display, sound generation, vibration or the like.

In a case of "No" in step 808, the controller 106 may further determine whether or not the predefined variable detected by the sensor 112 satisfies the predefined condition for requesting generation of aerosol. When the predefined variable satisfies the predefined condition, the controller 106 may cause the notifying part 108 to function in the first mode in step 810. In one example, the predefined variable may be a pressure or flow rate, and the predefined condition may include the pressure or the flow rate having a predetermined value for detecting the start of puff, or more. In another example, the predefined condition may include the pressure or the flow rate continuing for a predetermined time for detecting the start of puff. According to these characteristics, the notifying part 108 functions in the first mode not only based on the determination results in steps 804 and 808, but also based on that detection of the user trying to inhale by using the inhaler device 100. Accordingly, the user more easily notices that the first element (for example, the capsule 126) needs to be replaced.

When the capacity of the second element is less than the second threshold "Yes" in step 808), the process proceeds to step 812. In step 812, the controller 106 performs notification to the user in the second mode. For example, the controller 106 causes the notifying part 108 to function in the second mode.

According to the embodiment illustrated in FIG. 8, the notifying part 108 can be caused to function in different modes when only the capacity of the first element (for example, the capsule) is insufficient, and when the capacities of both of the first element and the second element (for example, the cartridge) are insufficient. Accordingly, the user can easily understand whether to replace only the first element, or to replace both of the first element and the second element.

The inhaler device 100 may include a plurality of elements including at least the first and second elements. In this case, the above described predefined condition may include a requirement that concerning each of the plurality of elements, the detected or estimated capacity is equal to or lower than a threshold set for the element. The controller 106 may be configured to cause the notifying part 108 to function when the predefined condition like this is satisfied. Further, the above described conditions may be stricter for the elements higher in frequency with which the operation for returning the elements into the state having the capacity necessary for continuous generation of aerosol, among the plurality of elements. In other words, the above described conditions may be looser for the elements lower in frequency with which the operation for returning the elements into the state having the capacity necessary for continuous generation of aerosol, among the plurality of elements. Further, the above described conditions may have a lower possibility of being satisfied for the elements higher in the above described frequency, among the plurality of elements. Alternatively, the above described conditions may include a larger number of requirements for the elements higher in the above described frequency among the plurality of elements. According to these characteristics, the notifying part 108 can be prevented from erroneously operating with respect to the elements which are frequently replaced, and the possibility of the user overlooking the operation of the notifying part 108 that urges replacement of the elements can be reduced.

The controller 106 may be configured to acquire the request for generation of aerosol. The above described condition for the elements highest in the above described frequency among the plurality of elements may include detection of the request. According to the characteristic, the element highest in the frequency of replacement or the like includes puff detection as the condition for causing the notifying part 108 to function. Accordingly, the notifying part 108 operates when the user clearly desires to perform inhaling, so that the possibility of the user overlooking the operation of the notifying part 108 can be further reduced.

The controller 106 may be configured to cause the notifying part 108 to function for a longer time when the above described condition is satisfied for the elements higher in the above described frequency among the plurality of elements. According to the characteristic, the user hardly overlooks the notifying part 108 operating, with respect to the elements high in frequency of replacement or the like.

When the notifying part 108 includes a light emitting element, the controller 106 may make setting so that light emission color of the light emitting element differs with respect to each of the plurality of elements. Thereby, the user can easily understand which element needs replacement or the like. The controller 106 may be also configured to set the light emission color of the light emitting element with respect to each of the plurality of elements based on the above described frequencies of the plurality of the elements. According to the characteristic, the user easily recognizes which element should be replaced or the like. The controller 106 further may be configured to set the light emission color of the light emitting element at a colder color for the elements higher in the above described frequency among the plurality of elements. By setting the color that is lit frequently at a cold color, the user can be urged to perform a replacement operation with a sense of everyday use without being excessively wary. The controller 106 also may be configured to control the light emitting element so that the light emission color of the light emitting element in the case of the above described condition being satisfied, and the light emission color of the light emitting element during generation of aerosol are the same, with respect to the element highest in the above described frequency among the plurality of elements. According to the characteristic, the user can be caused to understand that replacement or the like is necessary with respect to the element highest in frequency of replacement or the like (that is, frequency of notification to the user) without impairment of user experience. The controller 106 further may be configured to set the light emission color of the light emitting element at a warmer color for the element lower in the above described frequency among the plurality of elements. By setting the light emission color of the light emitting element at a warm color with respect to the elements low in frequency of replacement or the like, attention of the user can be strongly attracted when replacement timing of the elements which rarely need replacement or the like arrives.

In the process in FIG. 8, the frequency at which the operation for returning the element into the state having a necessary capacity for continuously generating aerosol or aerosol imparted with flavor (hereinafter, sometimes called "aerosol" collectively) for the first element is higher than the frequency for the second element. In one example, while the first element (capsule 126) is replaced five times, the second element (cartridge 104) can be replaced once.

In the process in FIG. 8, the capsule 126 may be the first element, and the battery 110 may be the second element. In one example, while the capsule 126 is replaced ten times, the battery 110 can be charged once.

Figure 9:
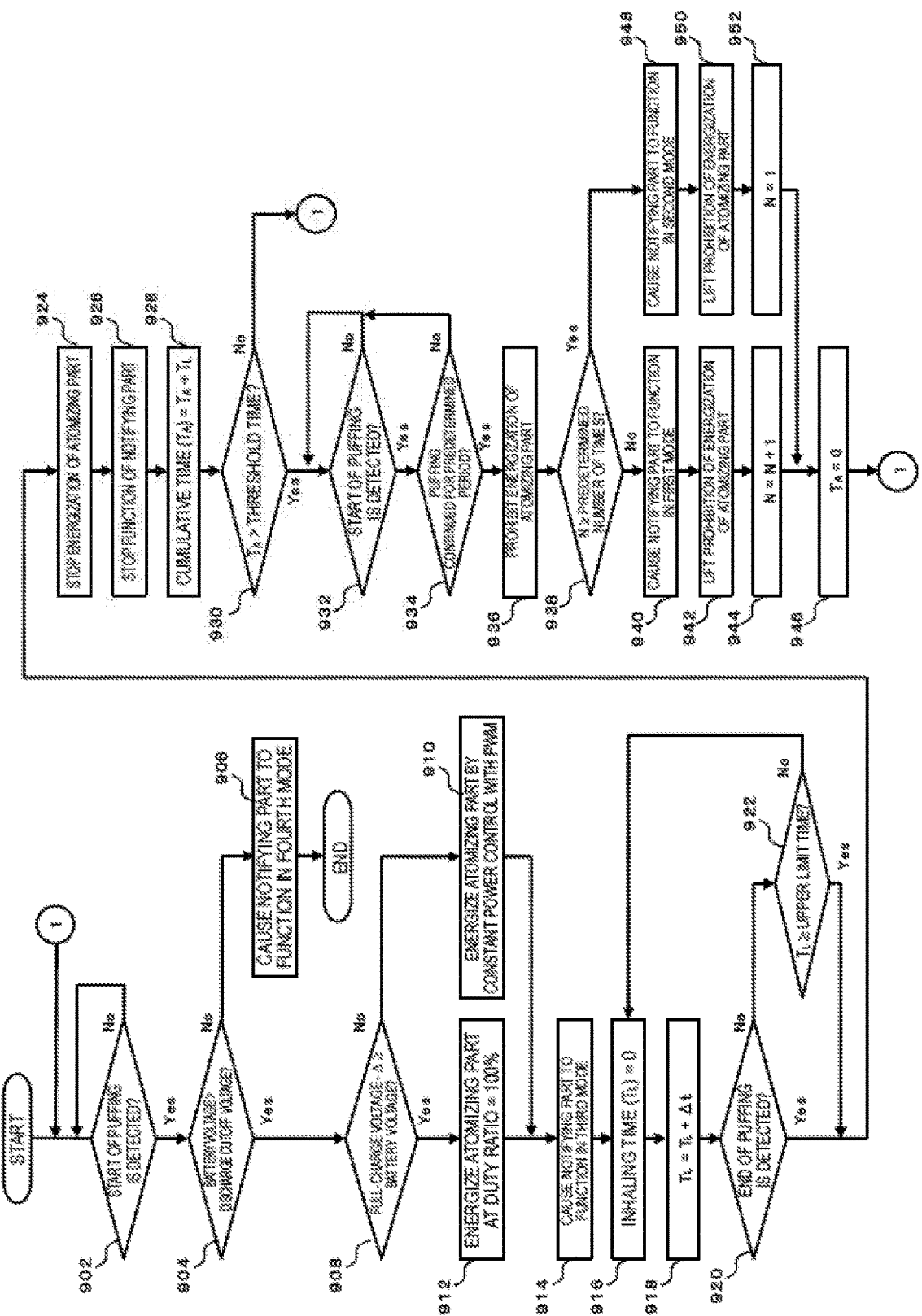
FIG. 9 is a flowchart showing, in detail, an example of the operation of the inhaler device according to the third embodiment of the present disclosure.

FIG. 9 is a flowchart illustrating an example of an operation of the inhaler device 100 according to the present embodiment in detail. Hereinafter, explanation will be performed by assuming that the controller 106 executes all of steps illustrated in FIG. 9. However, attention should be paid to that some of the steps in FIG. 9 may be executed other components in the inhaler device 100. Here, explanation will be made by assuming that the inhaler device has the configuration of the inhaler device 100B illustrated in FIG. 1B, and the inhaler device 100B has the battery 110, the cartridge 104 and the capsule 126 as elements, the capsule 126 corresponds to the first element in FIG. 8, and the cartridge 104 corresponds to the second element. Further, it is assumed that while the capsule 126 is replaced five times, the cartridge 104 can be replaced once.

A process is started in step 902. In step 902, the controller 106 determines whether or not start of puff of the inhaler device 100 by the user is detected. As one example, when the sensor 112 includes a pressure sensor or a flow rate sensor, the controller 106 may determine that puff is started when the pressure or the flow rate acquired from the sensor 112 exceeds a predefined value. The controller 106 further may determine that puff is started when a duration in which the pressure or the flow rate is detected by the sensor 112 exceeds a predefined duration. In another example, the inhaler device 100 may include a button for start, and the controller 106 may determine that puff is started when the button is pressed. When start of puff is not detected ("No" in step 902), the process returns to before step 902. When start of puff is detected ("Yes" in step 902), the process proceeds to step 904.

In step 904, the controller 106 determines whether or not the voltage of the battery 110 is larger than a threshold voltage (discharge cutoff voltage (for example, 3.2 V) or the like). When the voltage of the battery 110 is equal to or lower than the discharge cutoff voltage ("No" in step 904), the process proceeds to step 906. In step 906, the controller 106 causes the notifying part 108 to function in the fourth mode. In one example, in a case of the notifying part 108 including a LED, the fourth mode may include flashing the LED in red for 5.4 seconds. In another example, in a case of the notifying part 108 including a vibrator, the fourth mode may include vibrating the vibrator for 5.4 seconds. Thereafter, the process is ended. When the voltage of the battery 110 is larger than the discharge cutoff voltage on the other hand ("yes" in step 904), the process proceeds to step 908.

The processes in steps 908 to 912 are similar to the processes in step 308 to 312, so that explanation will be omitted here.

The process proceeds to step 914, and the controller 106 causes the notifying part 108 to function in the third mode. The third mode is an operation mode of the notifying part 108 at the time of the user performing normal inhaling by using the inhaler device 100B. In one example, in a case of the notifying part 108 including a LED, the controller 106 may steadily light the LED in blue, in step 914.

The processes in steps 916 to 928 are similar to the processes in steps 316 to 328 in FIG. 3, so that explanation will be omitted here.

Step 930 is one example of step 804 in FIG. 8 concerning the capsule 126 as the first element of the inhaler device 100B. In step 930, the controller 106 determines whether or not the cumulative time $T_A$ is larger than a predetermined threshold time. The threshold time can be a cumulative time of inhaling to the inhaler device 100B in which the capacity of the capsule 126 (for example, the residual amount of the flavor and taste component included in the flavor source 128) is below the value necessary to generate aerosol imparted with sufficient flavor. The threshold time may be stored in the memory 114 or the like in advance. When $T_A$ is equal to or shorter than the threshold time ("No" in step 930), the capacity of the capsule 126 is determined as the first threshold or more, and the process returns to before step 902. When the $T_A$ is larger than the threshold time ("Yes" in step 930), the capacity of the capsule 126 is determined as less than the first threshold, and the process proceeds to step 932.

The processes in steps 932 to 936 are similar to the processes in steps 332 to 336 in FIG. 3. A condition at a time of start of puff being determined as detected in step 932 may be stricter than the condition at the time of start of puff being determined as detected in step 902. Alternatively, a possibility that the condition at the time of start of puff being determined as detected in step 932 is satisfied may be lower than the possibility that the condition at the time of start of puff being determined as detected in step 902 is satisfied. In one example, the above described condition may include detection of a variable (for example, a pressure or flow rate) having an absolute value exceeding a predefined value. At this time, a predefined value used in determination in step 932 may be larger than the predefined value used in determination in step 902. The above described condition at the time of start of puff being determined as detected further may include puff continuing for a predetermined time in step 934. In one example, the above described condition may include detection of the variable (for example, the pressure) exceeding the predefined duration. When determination using the duration like this is also performed in step 902, the duration used in determination in step 934 may be longer than the duration used in determination in step 902. According to these characteristics, in an ordinary inhaling, response of aerosol generation to the puff operation by the user is made favorable, and an inhaling experience without a sense of discomfort can be provided. In addition, when the capacity of the capsule 126 is less than the first threshold value, the inhaler device 100 can be prevented from erroneously performing an ordinary operation due to background noise.

The process proceeds to step 938. Step 938 is one example of step 808 in FIG. 8 concerning the cartridge 104 as the second element of the inhaler device 100B. In step 938, N represents the number of times the capsule 126 is replaced. In step 938, "predetermined number of times" indicates the number of times the capsule 126 should be replaced while the cartridge 104 is replaced once. As described above, in the example in FIG. 9, the capsule 126 is replaced five times while the cartridge 104 is replaced once, so that the predetermined number of times in this case is five. Accordingly, in a case of N≥5, both the capsule 126 and the cartridge 104 need to be replaced, and when N is smaller than five, only the capsule 126 needs to be replaced, but the cartridge 104 does not need to be replaced.

In step 938, the controller 106 determines whether or not N is the predetermined number of times (in this case, five) or more. N may be stored in the memory 114. When N is less than the predetermined number of times ("No" in step 938), it corresponds to "No" in step 808 in FIG. 8. That is, at this time, the capacity of the capsule 126 which is the first element is less than the first threshold, but the capacity of the cartridge 104 which is the second element is the second threshold or more. In this case, the process proceeds to step 940. In step 940, similarly to step 810 in FIG. 8, the controller 106 causes the notifying part 108 to function in the first mode. In one example, in the case of the notifying part 108 including the light emitting element such as a LED, the first mode may include flashing the light emitting element in blue for 40 seconds. In another example, in the case of the notifying part 108 including a vibrator, the first mode may include vibrating the vibrator for two seconds.

When the notifying part 108 is caused to function in the first mode, the controller 106 may stop generation of aerosol. This may be realized by the process in step 936. For example, the controller 106 prohibits energization to the atomizing part 118. Since aerosol is not generated, attention of the user can be aroused, and the user can more easily notice that the capsule 126 needs to be replaced. In addition, incomplete aerosol can be prevented from being generated when the residual amount of the capsule 126 becomes insufficient, so that the inhaling experience of the user can be prevented from being impaired.

When the notifying part 108 includes a light emitting element, light emission colors of the light emitting element may be the same, and light emitting manners of the light emitting element may be different, in the first mode in step 940 and the third mode in step 914. Alternatively, the light emission colors of the light emitting element may be different, and the light emitting manners of the light emitting element may be the same, in the first mode and the third mode. Alternatively, in the first mode and the third mode, both the light emission colors and the light emitting manners of the light emitting element may be different. According to these characteristics, the user can be caused to recognize that some abnormality relating to inhaling occurs when the capacity of the capsule 126 becomes insufficient, and the user can be easily urged to replace the capsule 126.

The process proceeds to step 942, and the controller 106 cancels prohibition of energization to the atomizing part 118. At this time, the controller 106 may estimate that the capacity of the capsule 126 returns to a predetermined value (for example, a sufficient value to generate aerosol or aerosol imparted with flavor). The notification that is hardly overlooked by the user is already performed by the notifying part 108, so that after completion of the function of the notifying part 108 in the first mode, a provability of the capsule 126 insufficient in capacity being replaced or the like is high. According to the above described characteristic, it is not necessary to use control logic and elements for fitting detection and switch that are used for only the purpose of detecting whether or not replacement or the like of the capsule 126 is performed. Further, precision of count of the cumulative time and the number of times of replacement can be enhanced.

After the function of the notifying part 108 in the first mode is finished, the controller 106 also may count the number of times the capacity of the capsule 126 returns to the predetermined value. According to the characteristic, the number of times of replacement of the above described element that is a useful parameter in estimating the product life of the inhaler device 100 and consumption degrees of the other elements can be counted without using the control logic and elements for fitting detection and switch which are used for only the purpose of detecting whether or not replacement or the like of the element is performed.

The process proceeds to step 944, and the controller 106 increments N by 1. Thereby, the number of times of the capsule 126 being replaced increases by 1. In step 946, the controller 106 resets the cumulative time $T_A$ (sets to 0).

When N is the predetermined number of times in step 938 ("yes" in step "938"), it corresponds to "Yes" in step 808 in FIG. 8. That is, at this time, the capacity of the capsule 126 which is the first element is less than the first threshold value, and the capacity of the cartridge 104 which is the second element is less than the second threshold. Accordingly, both the capsule 126 and the cartridge 104 need to be replaced. In this case, the process proceeds to step 948. In step 948, the controller 106 causes the notifying part 108 in the second mode as in step 812 in FIG. 8. In one example, in the case of the notifying part 108 including a light emitting element such as a LED, the second mode may include flashing the light emitting element in green for 60 seconds. In this way, the controller 106 may be configured to cause the light emitting element of the notifying part 108 to emit light in different light emission colors in the first mode in step 940 and the second mode in step 948. According to the characteristic, the light emission color of the light emitting element changes when only the capsule 126 needs to be replaced and when both the capsule 126 and the cartridge 104 need to be replaced, so that the user easily understands which element needs to be replaced.

The controller 106 may be configured to set the light emission color of the light emitting element in the first mode at a colder color as compared with the light emission color in the second mode. Thereby, when only the capsule 126 needs to be replaced, the light emitting element emits light in a cold color. Accordingly, the user easily recognizes that a steady replacement operation is required, and can more easily understand whether only the capsule 126 needs to be replaced, or whether both of the capsule 126 and the cartridge 104 need to be replaced.

The controller 106 may be configured to cause the notifying part 108 to function for times of different lengths in the first mode and the second mode. Thereby, it can be more easily understandable whether only the capsule 126 needs to be replaced, or whether both of the capsule 126 and the cartridge 104 need to be replaced. The controller 106 may be configured to make the time in which the notifying part 108 is caused to function in the first mode shorter as compared with the time in which the notifying part 108 is caused to function in the second mode. Thereby, when only the capsule 126 needs to be replaced, the time in which the notifying part 108 functions becomes short. Accordingly, it becomes easy to cause the user to recognize that the operation that is completed in a short time is needed. Further, it becomes more easily understandable whether only the capsule 126 needs to be replaced, or both of the capsule 126 and the cartridge 104 need to be replaced.

In another example, in the case of the notifying part 108 including a vibrator, the second mode may include vibrating the vibrator for 60 seconds.

The process proceeds to step 950, and the controller 106 cancels prohibition of energization to the atomizing part 118. The process is similar to the process in step 942.

The process proceeds to step 952, and the controller 106 sets N to 1. Thereby, the number of times the capsule 126 is replaced is reset to 1. Thereafter, the process proceeds to step 946.

The controller 106 may be configured to interrupt the function of the notifying part 108 when at least one element of the plurality of elements is detached. In the example in FIG. 9, in a case of the cartridge 104 and the capsule 126 being detachable, the controller 106 may interrupt the function of the notifying part 108 when one or both of them is or are detached.

In the aforementioned explanation, the third embodiment of the present disclosure is described as the inhaler device having the configuration illustrated in FIG. 1A or FIG. 1B and the method illustrated in FIG. 8 or FIG. 9. However, it is understandable that when the present disclosure is executed by the processor, the third embodiment can be carried out as a program that causes the processor to execute the method illustrated in FIG. 8 or FIG. 9, or as a computer-readable storage medium that stores the program.

The embodiments of the present disclosure are described thus far, and it should be understood that these embodiments are only illustration, and do not limit the scope of the present disclosure. It should be understood that modification, addition, alteration and the like of the embodiments can be properly performed without departing from the gist and the scope of the present disclosure. The scope of the present disclosure should not be limited by any of the aforementioned embodiments, but should be specified by only the claims and the equivalents of the claims.

REFERENCE SIGNS LIST 100A, 100B • • • Inhaling device, 102 • • • First member, 104 • • • Second member, 106 • • • Controller, 108 • • • Notifying part, 110 • • • Battery, 112 • • • Sensor, 114 • • • Memory, 116 • • • Reservoir, 118 • • • Atomizing part, 120 • • • Air intake channel, 121 • • • Aerosol flow path, 122 • • • Suction port part, 124 • • • Arrow, 126 • • • Third member, 128 • • • Flavor source

What is claimed:

1. An inhaler device comprising:
a first element configured to consume a first accumulated capacity to contribute to generation of aerosol;
a second element configured to consume a second accumulated capacity to contribute to generation of the aerosol;
a light emitting diode (LED) configured to output a notification to an inhaler of the aerosol; and
circuitry configured to
cause the LED to function in a first mode when the first accumulated capacity, detected or estimated, concerning the first element is smaller than a first threshold and the second accumulated capacity, detected or estimated, concerning the second element is equal to or larger than a second threshold; and
cause the LED to function in a second mode different from the first mode when the first accumulated capacity is smaller than the first threshold and the second accumulated capacity is smaller than the second threshold, wherein
a rate at which the first element consumes the first accumulated capacity to contribute to the generation of the aerosol is greater than a rate at which the second element consumes the second accumulated capacity to contribute to the generation of the aerosol.

2. The inhaler device of claim 1, wherein
the circuitry is configured to cause the LED to emit light in different colors in the first mode and the second mode.

3. The inhaler device of claim 2, wherein
the circuitry is configured to set a light emission color of the LED in the first mode to a cold color.

4. The inhaler device of claim 1, wherein
the circuitry is configured to cause the LED to function for different durations of time in the first mode and the second mode.

5. The inhaler device of claim 4, wherein
the controller is configured to set a time for causing the LED to function in the first mode for a shorter duration of time compared with the duration of time in the second mode.

6. The inhaler device of claim 1, further comprising:
a sensor configured to detect a predefined variable, wherein
the circuitry is configured to cause the LED to function in the first mode when the first accumulated capacity is smaller than the first threshold, the second accumulated capacity is equal to or larger than the second threshold, and the predefined variable satisfies a condition for generation of the aerosol.

7. The inhaler device of claim 6, wherein
the circuitry is configured to perform control to stop generation of the aerosol when causing the LED to function in the first mode.

8. The inhaler device of claim 6, wherein
the condition corresponds to a higher threshold when the first accumulated capacity is smaller than the first threshold than when the first accumulated capacity is equal to or larger than the first threshold.

9. The inhaler device of claim 6, wherein
a likelihood that the condition is satisfied when the first accumulated capacity is smaller than the threshold is lower than a likelihood that the condition is satisfied when the first accumulated capacity is equal to or larger than the threshold.

10. The inhaler device of claim 8, wherein
the condition includes detection of the variable exceeding a duration of time, and the duration of time when the first accumulated capacity is smaller than the first threshold is longer than the duration of time when the first accumulated capacity is equal to or larger than the first threshold.

11. The inhaler device of claim 8, wherein
the condition includes detection of the variable having an absolute value exceeding a value, and the value when the first accumulated capacity is smaller than the first threshold is larger than the value when the first accumulated capacity is equal to or larger than the first threshold.

12. The inhaler device of claim 6, wherein
the circuitry is configured to cause the LED to function in a third mode during the generation of the aerosol, wherein
light emission colors of the LED in the first mode and the third manner are same, and light emission patterns of the LED in the first mode and the third manner are different.

13. The inhaler device of claim 6, wherein
the circuitry is configured to cause the LED to function in a third mode during the generation of the aerosol, wherein
light emission colors of the LED in the first mode and the third manner are different, and light emission patterns of the LED in the first mode and the third mode are the same.

14. The inhaler device of claim 6, wherein
the circuitry is configured to set the first accumulated capacity to a predetermined value after the function of the LED in the first mode ends.

15. The inhaler device of claim 6, wherein
the circuitry is configured to count a number of times the first accumulated capacity returns to a predetermined value after the function of the LED in the first mode ends.

16. The inhaler device of claim 1, wherein
the first element is a reservoir configured to retain liquid that is used to generate the aerosol, and the first accumulated capacity corresponds to an amount of liquid held by the reservoir, and
the second element is an atomizer configured to draw power from a battery to generate the aerosol, and the second accumulated capacity corresponds to an amount of power remaining in the battery.

17. The inhaler device of claim 1, wherein
the first element is an atomizer configured to draw power from a battery to generate the aerosol, and the first accumulated capacity corresponds to an amount of power remaining in the battery, and
the second element is a reservoir configured to retain liquid that is used to generate the aerosol, and the second accumulated capacity corresponds to an amount of liquid held by the reservoir.

18. The inhaler device of claim 1, wherein
the first element is a flavor source configured to retain flavoring substances used in generating the aerosol, and the first accumulated capacity corresponds to an amount of flavoring substances by the flavor source, and
the second element is a reservoir configured to retain liquid that is used to generate the aerosol, and the second accumulated capacity corresponds to an amount of liquid held by the reservoir.

19. An inhaler device comprising:
an atomizer configured to consume a first accumulated capacity and a second accumulated capacity to generate aerosol;
a light emitting diode (LED) configured to output a notification to an inhaler of the aerosol; and
circuitry configured to
  cause the LED to function in a first mode when the first accumulated capacity, detected or estimated, is smaller than a first threshold and the second accumulated capacity, detected or estimated, is equal to or larger than a second threshold; and
  cause the LED to function in a second mode different from the first mode when the first accumulated capacity is smaller than the first threshold and the second accumulated capacity is smaller than the second threshold, wherein
a rate at which the atomizer consumes the first accumulated capacity to generate the aerosol is greater than a rate at which the atomizer consumes the second accumulated capacity to contribute to generate the aerosol.

20. A non-transitory computer-readable medium including computer program instructions, which when executed by a processor of an inhaler device including an atomizer configured to consume a first accumulated capacity and a second accumulated capacity to generate aerosol, and a light emitting diode (LED) configured to output a notification to an inhaler of the aerosol, causes the inhaler device to:
  control the LED to function in a first mode when the first accumulated capacity, detected or estimated, is smaller than a first threshold and the second accumulated capacity, detected or estimated, is equal to or larger than a second threshold; and
  control the LED to function in a second mode different from the first mode when the first accumulated capacity is smaller than the first threshold and the second accumulated capacity is smaller than the second threshold, wherein
a rate at which the atomizer consumes the first accumulated capacity to generate the aerosol is greater than a rate at which the atomizer consumes the second accumulated capacity to contribute to generate the aerosol.

* * * * *